United States Patent
Brown et al.

(10) Patent No.: US 11,459,357 B2
(45) Date of Patent: Oct. 4, 2022

(54) POLYMYXIN COMPOUNDS

(71) Applicant: SPERO THERAPEUTICS, INC., Cambridge, MA (US)

(72) Inventors: Pamela Brown, Reading (GB); Michael Dawson, Reading (GB); Mona Simonovic, Reading (GB); Steven Boakes, Reading (GB); Esther Duperchy, Reading (GB); Dean Rivers, Reading (GB); Roy Lester, Reading (GB); Scott Coleman, Cambridge, MA (US)

(73) Assignee: SPERO THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 17/253,426

(22) PCT Filed: Jun. 25, 2019

(86) PCT No.: PCT/EP2019/066819
§ 371 (c)(1),
(2) Date: Dec. 17, 2020

(87) PCT Pub. No.: WO2020/002325
PCT Pub. Date: Jan. 2, 2020

(65) Prior Publication Data
US 2021/0246169 A1  Aug. 12, 2021

Related U.S. Application Data

(60) Provisional application No. 62/689,602, filed on Jun. 25, 2018.

(51) Int. Cl.
| | |
|---|---|
| *A61K 38/12* | (2006.01) |
| *C07K 7/62* | (2006.01) |
| *A61K 38/00* | (2006.01) |

(52) U.S. Cl.
CPC ............... *C07K 7/62* (2013.01); *A61K 38/12* (2013.01); *A61K 38/00* (2013.01)

(58) Field of Classification Search
CPC ................................. A61K 38/12; C07K 7/62
See application file for complete search history.

(56) References Cited

U.S. PATENT DOCUMENTS

| | | | |
|---|---|---|---|
| 4,510,132 | A | 4/1985 | Vaara |
| 5,565,423 | A | 10/1996 | Sandow et al. |
| 5,767,068 | A | 6/1998 | Vandevanter et al. |
| 8,329,645 | B2 | 12/2012 | Vaara et al. |
| 8,343,912 | B2 | 1/2013 | Leese |
| 8,415,307 | B1 | 4/2013 | Curran et al. |
| 9,234,006 | B2 | 1/2016 | Saadi et al. |

(Continued)

FOREIGN PATENT DOCUMENTS

| | | |
|---|---|---|
| CN | 101851270 A | 10/2010 |
| EP | 0571921 A2 | 12/1993 |

(Continued)

OTHER PUBLICATIONS

ChemFiles, "Peptide Synthesis" (2007) vol. 7, No. 2, 20 pages.

(Continued)

*Primary Examiner* — Jeffrey E. Russel
(74) *Attorney, Agent, or Firm* — Cantor Colburn LLP

(57) ABSTRACT

The invention provides a polymyxin compound of formula (I) and salts, solvates and protected forms thereof, pharmaceutical compositions comprising the compounds of formula (I), and the use of the compounds and compositions in methods of treatment, such as methods for the treatment of microbial infections. The compounds of formula (I) are represented thus:

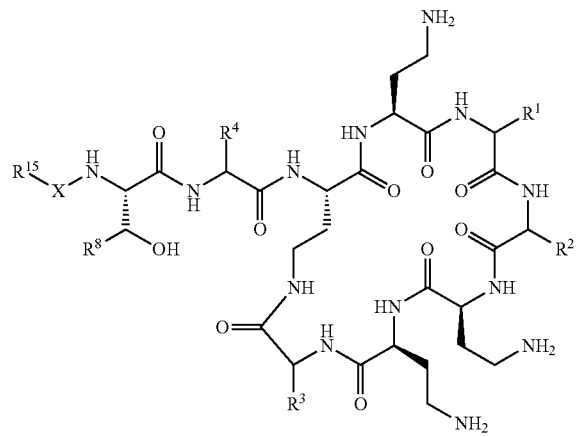

wherein —$R^{15}$ is a group:

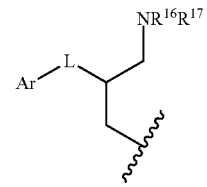

and —$R^{16}$ is hydrogen; —$R^{17}$ is hydrogen -L- is a covalent bond or methylene; and —Ar is optionally substituted aryl. The groups —X—, —$R^1$, —$R^2$, —$R^3$, —$R^4$, and —$R^8$ are as defined herein.

14 Claims, No Drawings

(56) References Cited

U.S. PATENT DOCUMENTS

| | | | |
|---|---|---|---|
| 10,407,467 | B2 | 9/2019 | Brown et al. |
| 2001/0021697 | A1 | 9/2001 | Lowenstein et al. |
| 2008/0207874 | A1 | 8/2008 | Leese et al. |
| 2008/0279820 | A1 | 11/2008 | Hicks et al. |
| 2008/0287345 | A1 | 11/2008 | Vaara et al. |
| 2009/0215677 | A1 | 8/2009 | Vaara et al. |
| 2009/0239792 | A1 | 9/2009 | Vaara et al. |
| 2010/0160215 | A1 | 6/2010 | Leese |
| 2012/0316105 | A1 | 12/2012 | Magee et al. |
| 2016/0222061 | A1 | 8/2016 | Brown et al. |
| 2017/0073373 | A1 | 3/2017 | Brown et al. |
| 2018/0030092 | A1 | 2/2018 | Brown et al. |
| 2021/0221848 | A1 | 7/2021 | Brown et al. |

FOREIGN PATENT DOCUMENTS

| | | | |
|---|---|---|---|
| GB | 2128617 | A | 5/1984 |
| WO | 8800950 | A2 | 2/1988 |
| WO | 2008017734 | A1 | 2/2008 |
| WO | 2009098357 | A1 | 8/2009 |
| WO | 2010075416 | A1 | 1/2010 |
| WO | 2010029196 | A1 | 3/2010 |
| WO | 2010130007 | A1 | 11/2010 |
| WO | 2012051663 | A1 | 4/2012 |
| WO | 2012168820 | A1 | 12/2012 |
| WO | 2013072695 | A1 | 5/2013 |
| WO | 2014188178 | A1 | 11/2014 |
| WO | 2015135976 | A1 | 9/2015 |
| WO | 2015149131 | A1 | 10/2015 |
| WO | 2016083531 | A1 | 6/2016 |
| WO | 2016166103 | A1 | 10/2016 |
| WO | 2017054047 | A1 | 4/2017 |
| WO | 2020014501 | A1 | 1/2020 |

OTHER PUBLICATIONS

European Patent Office, Examination Repod for Application No. EP 12797961.5, dated Jun. 1, 2015, 6 pages.
International Preliminary Report on Patentability of International Application No. PCT/EP2015/077821, international filing date—Nov. 26, 2015; dated May 30, 2017, 7 pages.
International Search Report and the Written Opinion of the International Searching Authority for International Application No. PCT/EP2015/055046, dated Jul. 10, 2015, 12 pages.
International Search Report and the Written Opinion of the International Searching Authority for International Application No. PCT/EP2015/077821, dated Apr. 19, 2016, 13 pages.
International Search Report and the Written Opinion of the International Searching Authority for International Application No. PCT/GB2012/052844, dated Feb. 11, 2013, 17 Pages.
International Search Report and the Written Opinion of the International Searching Authority for International Application No. PCT/GB2014/051547, dated Dec. 8, 2014, 12 pages.
International Search Report of PCT/EP2015/077821, filed Nov. 26, 2015, dated Apr. 19, 2016, 6 pages.
Search Report of Application No. GB1421019.9, dated Aug. 21, 2015, 4 pages.
Search Report on Application No. GB1309248.1, dated Nov. 11, 2013, 5 pages.
Search Report on Application No. GB1404301.2, dated Dec. 8, 2014, 5 pages.
Search Report on Application No. GB1421020.7, dated Aug. 24, 2015, 5 pages.
Taiwan Intellectual Property Office, First Office Action for Application No. 101142961, dated May 12, 2016, 5 pages.
The Eurasian Patent Organization, First Office Action for Application No. 201490634, dated Jun. 3, 2015, 4 pages.
The Eurasian Patent Organization, Second Office Action for Application No. 201490634, dated Oct. 12, 2015, 2 pages.
De Visser et al., "Solid-phase synthesis of polymyxin B1 and analogues via a safety-catch approach" J. Peptide Res., (2003), vol. 61, 298-306.
Diaz et al., "Fast and Efficient Access to a Family of Multifunctional 1, 3, 5-Trisubstituted Piperidines, Synthetic Communications: An International Journal for Rapid Communication of Synthetic Organic Chemistry", (2008), 38:16 2799-2813.
Gallou et al., "Practical Synthesis of Unsymmetricial Ureas from Isopropenyl Carbamates", J. Org. Chem. (2005), vol. 70, (No. 17), 6960-6963.
Katsuma et al., "Antimicrobial Activity of Des-Fatty Acyl-Polymyxin B Decapeptide N-Terminal Analogs", Peptide Science, (2004), 549-550.
Katsuma et al., "Development of Des-Fatty Acyl-Polymyxin B Decapeptide Analogs with Pseudomonas aeruginosa-Specific Antimicrobial Activity" Chem. Pharm. Bull., (2009), vol. 57, (No. 4) 332-336.
Kimura et al., "Polymyxin B Octapeptide and Polymyxin B Heptapeptide are potent outer membrane permeability-increasing agents" The Journal of Antiboitics, (1992), vol. 45, (No. 5), 742-749.
Li et al., "Use of High-Performance Liquid Chromatography to Study the Pharmacokinetics of Colistin Sulfate in Rats following Intravenous Administration" Antimicrobial Agents and Chemotherapy, (2003), vol. 47, (No. 5) 1766-1770.
Magee et al., "Discovery of Dap-3 Polymyxin Analogs for the Treatment of Multidrug-Resistant Gram-negative Nosocomial Infections", Journal of Medicinal Chemistry, (2013), 1-55.
O'Dowd et al., "Preparation of tetra-Boc-protected polymyxin B nonapeptide" Tetrahedron Letters 48, (2007), 2003-2005.
Okimura et al., "Antimicrobial Activity of Various Aminocyclohexylcarbonyl-polymyxin B (2-10) Derivatives", Peptide Science (2008), 243-244.
Petrosillo, "Colistin Monotherapy vs. Combination Therapy: Evidence from Microbiological, Animal and Clinical Studies" European Society of Clinical Microbiology and Infectious Diseases, (2008) vol. 14, (No. 9), 816-827.
Bergen et al., "Colistin Methanesulfonate Is an Inactive Prodrug of Colistin against Pseudomonas aerginosa," Antimicrobial Agents and Chemotherapy, (2006), vol. 50, (No. 6), 1953-1958.
Bergen et al., "Pharmacokinetics and pharmacodynamics of "old" polymyxins: What is new?" Diagnostic Microbiology and Infectious Disease, (2012), vol. 74, 213-223.
Cleveland Clinic, "Polymyxin B Injection," Online: https://my.cleveland.org/health/drugs/20275-polymyxin-b-injection, accessed (2020), 7 pages.
Gallardo-Godoy et al., "Activity and Predicted Nephrotoxicity of Synthetic Antibiotics Based on Polymyxin B," Journal of Medicinal Chemistry, (2016), vol. 59, 1068-1077.
Kline et al., "Synthesis and characterization of the colistin peptide polymyxin E1 and related antimicrobial peptides," Journal of Peptide Res., (2001), vol. 57, 175-187.
Tsubery et al., "Modulation of the Hydrophobic Domain of Polymyxin B Nonapeptide: Effect on Outer-Membrane Permeabilization and Lipopolysaccharide Neutralization," Molecular Pharmacology, (2002), vol. 62, (No. 5), 1036-1042.
Quale et al., "Activity of Polymyxin B and the Novel Polymyxin Analogue CB-182,804 Against Contemporary Gram-Negative Pathogens in New York City", Microbial Drug Resistance, (2012), Vol. (No. 00), 1-5.
Sato et al., "Des-Fatty Acyl-Polymyxin B Decapeptide Analogs with Antimicrobial Activity Specifically against Pseudomonas Aeruginosa", Peptide Society, (2007), 307-308.
Sato et al., "Novel Des-Fatty Acyl-Polymyxin B Derivatives with Pseudomonas aeruginosa-Specific Antimicrobial Activity", Chem. Pharm. Bull., (2011), vol. 59 (No. 5), 597-602.
Shecter et al., "N-[(2-Sulfo)-9-fluorenylmethoxycarbonyl]3-gentamicin C1 Is a Long-Acting Prodrug Derivative", Journal of Medicincal Chemistry, (2002), vol. 45. (No. 19), 4264-4270.
Tsubery et al., "N-terminal modifications of Polymyxin B nonapeptide and their effect on antibacterial activity", Peptides (2001), vol. 22, 1675-1681.
Vaara et al., "A Novel Polymyxin Derivate That Lacks the Fatty Acid Tail and Carries Only Three Positive Charges Has Strong

(56) References Cited

OTHER PUBLICATIONS

Synergism with Agents Excluded by the Intact Outer Membrane", Antimicrobial Agents and Chemotherapy, (2010), vol. 54, (No. 8), 3341-3346.

Vaara et al., "Novel Polymyxin Derivatives Carrying Only Three Positive Charges Are Effective Antibacterial Agents" Antimicrobial Agents and Chemotherapy, (2008), vol. 52, (No. 9), 3229-3236.

Vaara et al., "Susceptibility of carbapenemase-producing strains of Klebsiella pneumoniae and *Escherichia coli* to the direct antibacterial activity of NAB739 and to the synergistic activity of NAB7061 with rifampicin and clarithromycin", Journal of Antimicrobial Chemotherapy, (2010), vol. 65, 942-945.

Varra "Agents that Increase the Permability of the Outer Membrane" Microbiological Reviews, (1992) vol. 56, (No. 3) 395-411.

Velkov et al., "Structure-Activity Relationships of Polymyxin Antibiotics" J. Med. Chem. (2010) vol. 53, (No. 5), 1898-1916.

Velko et al., "Teaching 'Old' Polymyxins New Tricks: New-Generation Lipopeptides Targeting Gram-Negative Superbugs" ACS Chemical Biology, (2014), (No. 9),1172-1177.

Voitenko et al., "Relationship between structure and histamine releasing action of polymyxin B and its analogues" Agents and Actions, (1990), vol. 30. (No. 1:2), 153-156.

Weinstein et al., "Selective Chemical Modifications of Polymyxin B", Bioorganic & Medicinal Chemistry Letters 8, (1998), 3391-3396.

Yamada et al., "Facile synthesis of Nα-protected-l-α,γ-diaminobutyric acids mediated by polymer-supported hypervalent iodine reagent in water", J. Peptide Res., (2004), vol. 64, 43-50.

Yousef et al., "Melatonin Attenuates Colistin-Induced Nephrotoxicity in Rats" Antimicrobial Agents and Chemotherapy, (2011), vol. 55, 4044-4049.

Kanazawa et al., "Contribution of Each Amino Acid Residue in Polymyxin B3 to Antimicrobial and Lipopolysaccharide Binding Activity", Chem. Pharm. Bull., (2009) vol. 57, (No. 3), 240-244.

Kato et al., "The Structure of Octapeptin D", The Journal of Antibiotics, (1980), vol. XXXIII, (No. 2), 186-191.

Shoji, et al., "The Structure of Polymyxin T1,"The Journal of Antibiotics, (1977), vol. XXX (No. 12), 1042-1048.

Okimura, K., et al., "Chemical Conversion of Natural Polymyxin B and Colistin to Their N-Terminal Derivatives" Bull. Chem. Soc. Japan, (2007), vol. 80, (No. 3), 543-552.

State Intellectual Property Office of China, First Office Action for Application No. 201280055987.6, dated Nov. 24, 2015, 6 pages.

United Kingdom Intellectual Property Office, CAS Search Results, tilted "Short fatty acid tail polymyxin derivatives and uses thereof" (2013) 68 Pages, Issued Nov. 11, 2013.

Koh et al., "Recent Advances in Synthetic Lipopeptides as Anti-Microbial Agents: Designs and Synthetic Approaches," Amino Acids (2017) vol. 49(10), pp. 1653-1677.

International Search Report and Written Opinion; International Application No. PCT/EP2019/066819; International Filing Date—Jun. 25, 2019; dated Oct. 24, 2019, 10 pages.

Ashenhurst, "Huckel's Rule: What Does 4n+2 Mean?"—Master Organic Chemistry, (2012), 3 pages.

Christe et al., "Halogen," Encyclopedia Britannica, www.britannica.com/science/halogen, (2020), 2 pages.

Cleveland Clinic, "Polymyxin B Injection," www.my.cleveland.org/health/drugs/20275-polymyxin-b-injection, (2020), 7 pages.

Kurtzhals et al., "Albumin Binding of Insulins Acylated With Fatty Acids: Characterization of the Ligand-Protein Interaction and Correlation Between Binding Affinity and Timing of the Insulin Effect in Vivo," Biochem. Journal, (1995), vol. 312, 725-731.

Merriam-Webster, "Halo," www.merriam-webster.com/dictionary/halo, (2020), 2 pages.

Seebach et al., "The World of Beta and Gamma Peptides Comprised of Homologated Proteinogenic Amino Acids and Other Components," Chemistry & Biodiversity (2004), vol. 1, 1111-1239.

The New World Encyclopedia, "Threonine," www.newworldencyclopedia.org/entry/Threonine, (2008), 3 pages.

Vaara, "Novel Derivatives of Polymyxins," Journal of Antimicrobial Chemotherapy, (2013), 68, 1213-1219.

Vaara, "Polymyxins and Their Novel Derivatives," Current Opinion in Microbiology, (2010), 13, 574-581.

POLYMYXIN COMPOUNDS

CROSS REFERENCE TO RELATED APPLICATIONS

This application is a National Stage application of PCT/EP2019/066819, filed Jun. 25, 2019, which claims priority to U.S. Provisional Application No. 62/689,602, filed Jun. 25, 2018, and all the benefits accruing therefrom under 35 U.S.C. § 119, each of which is incorporated by reference in its entirety.

FIELD OF THE INVENTION

The present invention relates to novel polymyxin compounds, pharmaceutical compositions comprising the compounds, and the use of the compounds and the pharmaceutical compositions for medical treatment, for example treatment of microbial infections, particularly infections by Gram-negative bacteria.

BACKGROUND

WO 2013/072695 and WO 2014/188178 describe polymyxin derivatives in which the N-terminal fatty acyl moiety and adjacent diaminobutyric acid moiety of Polymyxin B or Colistin are replaced by a terminal group having an amino substituent. Such derivatives have good antibacterial activity whilst having a reduced cytotoxicity.

WO 2015/135976 also describes polymyxin derivatives in which again the N-terminal fatty acyl moiety and adjacent diaminobutyric acid of Polymyxin B or Colistin are replaced by a terminal group having an amino substituent. Here, the specific position of the amino substituent and the placement of other substituents in the N-terminal moiety were shown to be important for strong antimicrobial activity across a range of key pathogens, such as *Escherichia coli, Klebsiella pneumoniae, Pseudomonas aeruginosa* and *Acinetobacter baumannii*. The compounds disclosed also retained a low cytotoxicity.

WO 2016/083531 describes polymyxin derivatives in which again the N-terminal fatty acyl moiety and adjacent diaminobutyric acid of Polymyxin B or Colistin are replaced by a terminal group having an amino substituent, such as those groups present in WO 2013/072695, WO 2014/188178 and WO 2015/135976. Additionally, the amino acid residue at positions 6 and/or 7 are substituted with respect to Polymyxin B and Colistin.

To be more useful for the parenteral therapy of systemic infections than the currently available polymyxins, new polymyxin derivatives must at least match the activity of these known polymyxins whilst having significantly lower renal toxicity in vivo.

SUMMARY OF THE INVENTION

In a general aspect, the invention provides compounds having a deacylated polymyxin core, such as a nonapetide core of Polymyxin B or Colistin with the amino acid residue at position 3 substituted with Dap, having a group —X—$R^{15}$, as defined herein, at its N terminal. Such compounds find use in a method of treatment or prophylaxis, optionally in combination with a second active agent. The compounds may be used to treat a microbial infection, such as a Gram-negative bacterial infection.

The compounds of the present invention are shown to have low cytotoxicity balanced with acceptable kidney drug levels after parenteral dosing. The compounds of the present invention are shown to be superior to both Polymyxin B, as well as modified polymyxin compounds known in the art, including those previously reported by the present applicant. This superiority is manifest in one or more of the following characteristics: lower cytotoxicity, acceptable kidney drug levels (i.e., acceptable renal toxicity, resulting from kidney drug levels are not high) after parenteral dosing, efficacy in mouse thigh and lung models, and/or superior MIC against pathogenic bacterial strains, while being equivalent to the prior art compounds in the others.

Typically the compounds known in the art exhibit one, or perhaps two of these advantageous characteristics, but not all. For example, it is now relatively common to find polymyxin compounds having lower cytotoxicity, but this lower cytotoxicity is often accompanied with a reduction in antibacterial activity. Further, compounds having a lower cytotoxicity may nevertheless be found within the kidney at high levels after dosing. Such compounds are therefore still toxic, and not useful in methods of medical treatment.

In a first aspect of the invention, there is provided a compound of formula (I), and pharmaceutically acceptable salts, solvates, protected forms and prodrug forms thereof. The compound of formula (I) is represented thus:

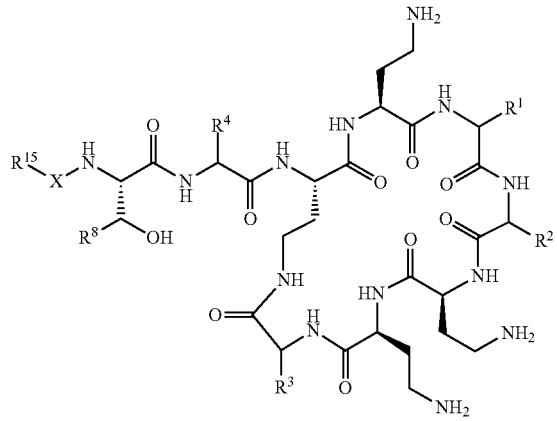

wherein:
- —X— represents —C(O)—;
- —$R^1$ together with the carbonyl group and nitrogen alpha to the carbon to which it is attached, is a phenylalanine, leucine, norleucine, valine or norvaline residue;
- —$R^2$ is $C_{1-4}$ alkyl optionally substituted with one hydroxyl group;
- —$R^3$ together with the carbonyl group and nitrogen alpha to the carbon to which it is attached, is a threonine residue;
- —$R^4$ together with the carbonyl group and nitrogen alpha to the carbon to which it is attached, is Dap, such as L-Dap;
- —$R^8$ is hydrogen or methyl; and
- —$R^{15}$ is a group:

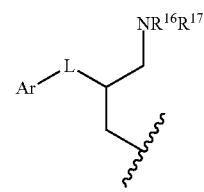

where:
- —$R^{16}$ is hydrogen;
- —$R^{17}$ is hydrogen;

-L- is a covalent bond or methylene (—CH$_2$—);

—Ar is optionally substituted aryl, such as substituted phenyl.

The compound of formula (I) may also be represented thus:

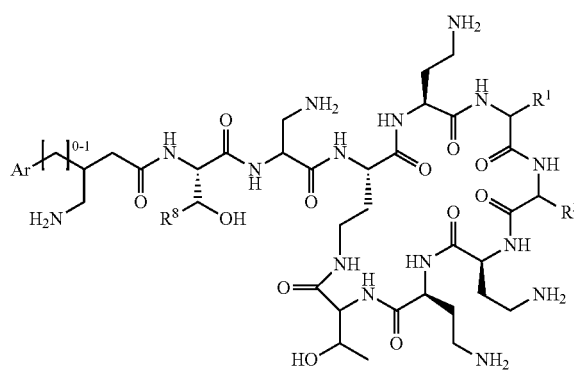

where —R$^1$, —R$^2$, —R$^8$ and —Ar have the same meanings as above, and pharmaceutically acceptable salts, solvates, protected forms and prodrug forms thereof.

The invention also provides a pharmaceutical composition comprising a compound of formula (I), optionally together with one or more pharmaceutically acceptable carriers.

In a further aspect there is provided a compound of formula (I), or a pharmaceutical composition comprising a compound of formula (I), for use in a method of treatment or prophylaxis.

In yet a further aspect there is provided a compound of formula (I), or a pharmaceutical composition comprising a compound of formula (I), for use in a method of treating a microbial infection.

The present invention also provides a method of treatment, the method comprising the step of administering a compound of formula (I), or a pharmaceutical composition comprising a compound of formula (I), to a subject in need thereof. The method may be for the treatment of a microbial infection.

A microbial infection may be a bacterial infection, such as a Gram-negative bacterial infection. The Gram-negative bacterial infection may be selected from the group consisting of *Escherichia* spp., *Klebsiella* spp., *Enterobacter* spp., *Salmonella* spp., *Shigella* spp., *Citrobacter* spp., and other Enterobacteriaceae, *Pseudomonas* spp., *Acinetobacter* spp., *Stenotrophomonas*, and *Legionella*.

The present invention also provides methods for the preparation of compounds of formula (I) as well as intermediate compounds for use in the preparation of the compounds of formula (I).

These and other aspects and embodiment of the invention are described in further detail below.

DETAILED DESCRIPTION OF THE INVENTION

The present invention provides compounds of formula (I), including the compounds of formula (II) and (III) as described in further detail below, for use in medical treatment, optionally together with a second active agent.

Broadly, the compounds of formula (I), (II) and (III) have a polymyxin core, which is a nonapeptide core, and a group —X—R$^{15}$ at the N terminal of the polymyxin core. The group —R$^{15}$ is a substituted γ-aminopropyl group. The γ-aminopropyl group is substituted at the β-position relative to the —X— moiety with an optionally substituted aryl or aralkyl group. The first amino acid residue in the exocyclic chain of the compounds of the invention—corresponding to position 3 in polymyxin—is a Dap residue (diaminopropionic acid), such as L-Dap, rather than a L-Dab residue (L-diaminobutyric acid), as present in Polymyxin B and Colistin.

The amino acid residues at positions 6 and 7 of the polymyxin compound (following the numbering used for polymyxin) may correspond to those amino acid residues present in Polymyxin B and Colistin. The amino acid residues at positions 6 and/or 7 may be substituted with different amino acid residues to those present within Polymyxin B and Colistin.

To be more useful for the parenteral therapy of systemic infections than the currently known series of polymyxin compounds, new polymyxin derivatives must at least match the antibacterial activity of those known polymyxin compounds whilst having significantly lower renal toxicity in vivo.

It has now been found that it is not sufficient for a polymyxin compound to exhibit lower cytotoxicity, as such is frequently not associated with reduced toxicity in vivo. Thus, the accumulation of the drug in the kidney and its clearance from there must also be favourable. In other words, the combination of cytotoxicity and kidney drug levels after parenteral dosing is what leads to a favourable in vivo toxicity profile.

This may be shown by way of the example comparisons shown in Table A below, where PMBN refers to the Polymyxin B nonapeptide core and PMEN refers to the Polymyxin E nonapeptide core, with the substitutions to the amino acid residues at positions 3 and 6 (according to Polymyxin numbering) shown, where appropriate (for example, Dap replacing Dab at position 3, and cyclohexylalanine (CHA) replacing phenylalanine at position 6).

TABLE A

| Compound | Structure | Cytotoxicity | Drug Level in Kidney | | Renal toxicity* |
|---|---|---|---|---|---|
| | | | 4 h | 16 h | |
| Polymyxin B | NH$_2$ ... PMBN | 1.0 | 128 | 18 | ++ |

TABLE A-continued

| Compound | Structure | Cytotoxicity | Drug Level in Kidney 4 h | Drug Level in Kidney 16 h | Renal toxicity* |
|---|---|---|---|---|---|
| Reference Example D77 WO 2015/135976 | PMEN-Dap$_3$ | 23** | 516 | 264 | ++++ |
| Reference Example 38 WO 2016/083531 | PMBN-Dap$_3$-CHA$_6$ | 9.2*** | 567 | 333 | +++ |
| Example 5 | PMBN-Dap$_3$ | 11.6 | 170 | 19 | +/− |

The cytotoxicity refers to measured IC$_{50}$ relative to that recorded for Polymyxin B against a HK-2 cell line. The drug level refers to the amount of compound (μg/g kidney) found in the kidney at 4 or 16 hours after a 17.2 mg/kg sc dose in a mouse.
*Compounds were dosed for either 4 doses 8 h apart at 25 mg free base/kg/dose or 4 days tid at 4 hour intervals at 17.2 mg free base/kg/dose. After dosing urine was collected for 16-24 h for determination of urinary biomarkers of renal toxicity (KIM-1, albumin, cystatin C). Compounds were graded as − (indistinguishable to vehicle control) to ++++ (strong response from all biomarkers).
**In WO 2015/135976 a figure of 13.3 was quoted for this compound (Example D77). This compound has now been tested twice further and the relative value calculated based on the value for PMB in the same experiment. The mean value was 23
***In WO 2016/083531 an IC$_{50}$ of 255 μg/mL is quoted for this compound (Example 38) as against 12 μg/mL for Polymyxin B. However, the figure for PMB used in that application was a median value from multiple experiments. The figure of 9.2 quoted here is by comparison with the IC$_{50}$ value for PMB determined in the same experiment The present applicant has previously disclosed in WO 2015/135976 polymyxin nonapeptides with an N-terminal γ-aminopropyl group substituted with a phenyl or benzyl moiety. However the phenyl or benzyl substituent is provided at the α-position, rather than β-position, relative to the —X— group. WO 2015/135976 also describes a polymyxin nonapeptide with an N-terminal β-aminoethyl group substituted at the α-position with a benzyl group. Here, the amino functionality is provided at the β-position rather than the γ-position, relative to the —X— group.

Whilst these known compounds show promising activity and moderately improved cytotoxicity compared to Polymyxin B, these compounds are inferior to the compounds of the present invention in that they do not display a combination of low cytotoxicity together balanced with acceptable kidney levels after dosage.

This is shown by way of the example comparisons shown in Table B below, where PMBN refers to the Polymyxin B nonapeptide core, with the substitutions to the amino acid residue at positions 3, where appropriate (for example, Dap replacing Dab at position 3).

TABLE B

| Compound | Structure | Cytotoxicity | Drug Level in Kidney (μg/g kidney, 4 h) | 4 hr kidney level/rel. cytotoxicity |
|---|---|---|---|---|
| Reference Compound D6 WO 2015/135976 | PMBN | 4.4* | 235 | 53 |

TABLE B-continued

| Compound | Structure | Cytotoxicity | Drug Level in Kidney (μg/g kidney, 4 h) | 4 hr kidney level/rel. cytotoxicity |
|---|---|---|---|---|
| Reference Compound** | 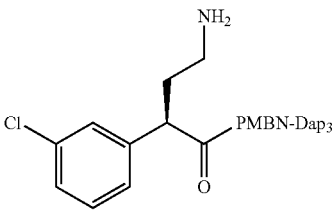 | 5.1 | 589 | 115 |
| Reference Compound** | 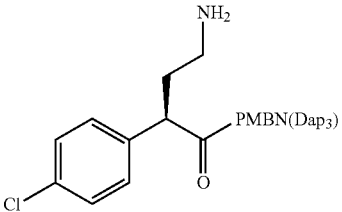 | 4.8 | 533 | 111 |
| Example 1 | 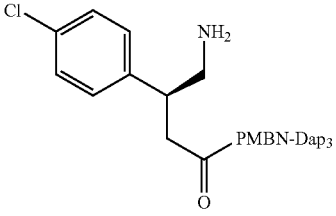 | 8.8 | 268 | 30 |
| Example 5 | 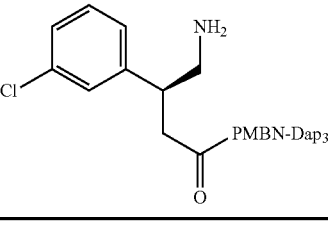 | 11.6 | 170 | 15 |

*This compound is example D6 in WO 2015/135976. The figure quoted there for the relative cytotoxicity was 3.7. This figure is the mean of two repeat determinations.
**The compounds of these Reference Examples may be prepared according to the methods descried in WO 2015/135976, the contents of which are hereby incorporated by reference in their entirety.

The present applicant has previously disclosed in WO 2016/083531 polymyxin nonapeptides with modified N-terminal groups, particularly those including β-aryl or β-aralkyl groups. However, these known compounds have a lipophilic amino acid residue at position 6, such as a cyclohexylalanine residue, whilst the compounds of the present case have, for example, a phenylalanine, leucine, norleucine, valine or norvaline residue at position 6. These known compounds again are inferior to the compounds of the current invention in view of the poor combination of cytotoxicity and kidney drug levels after dosage.

This is shown by way of the example comparisons shown in Table C below, where PMBN refers to the Polymyxin B nonapeptide core, with the substitutions to the amino acid residues at positions 3 and 6 shown, where appropriate (for example, Dap replacing Dab at position 3, and cyclohexylalanine (CHA) replacing phenylalanine at position 6).

TABLE C

| Compound | Structure | Cytotoxicity | Drug level in kidney (μg/g kidney, 4 h) | 4 hr kidney level/rel. cytotoxicity |
|---|---|---|---|---|
| Reference Compound 50 WO 2016/083531 | Cl-C6H4-CH(CH2-C(O)-PMBN-Dap3-CHA6)-CH2-NH2 | 7.4 | 463 | 63 |
| Reference Compound 58 WO 2016/083531 | C6H5-CH2-CH(CH2-C(O)-PMBN-Dap3-CHA6)-CH2-NH2 | 5.2 | 212 | 32 |
| Example 1 | Cl-C6H4-CH(CH2-C(O)-PMBN-Dap3)-CH2-NH2 | 8.8 | 268 | 30 |
| Example 9 | C6H5-CH2-CH(CH2-C(O)-PMBN-Dap3)-CH2-NH2 | 12.0 | 159 | 13 |

Compounds 50 and 58 are known from WO 2016/083531, and these are the compounds identified as Isomer 1 in that case.

Polymyxin Compounds

The compounds of formula (I) are N-terminal derivatives of the polymyxin nonapeptide series of compounds. The core of the compound of formula (I) is a derivative of a nonapeptide, such as the Polymyxin B nonapeptide (PMBN, Polymyxin B 2-10), where the amino acid residue at position 3 is substituted with Dap. Optionally the amino acid residues at positions 6 and/or position 7 are substituted with another amino acid, such as described herein. The compounds of formula (I) have a group —X—$R^{15}$ at the N terminal of the polymyxin core. This is described in detail below.

—$R^1$

The group —$R^1$, together with the carbonyl group and nitrogen alpha to the carbon to which it is attached, corresponds to the amino acid residue at position 6 in the polymyxin series of compounds.

The amino acid residue at position 6 may be the same as the amino acid residue at position 6 of Polymyxin B. That is, $R^1$ together with the carbonyl group and nitrogen alpha to the carbon to which it is attached may be a D-phenylalanine residue.

The amino acid residue at position 6 may the same as the amino acid residue at position 6 of Colistin. That is, $R^1$ together with the carbonyl group and nitrogen alpha to the carbon to which it is attached may a D-leucine residue.

In one embodiment, —$R^1$ together with the carbonyl group and nitrogen alpha to the carbon to which it is attached, is a phenylalanine, leucine, norleucine, valine or norvaline residue. The amino acid residue may be the D-form.

In one embodiment, —$R^1$ together with the carbonyl group and nitrogen alpha to the carbon to which it is attached, is an amino acid residue, such as a phenylalanine, leucine or norleucine residue. The amino acid residue may be the D-form.

In one embodiment, —$R^1$ together with the carbonyl group and nitrogen alpha to the carbon to which it is attached is a phenylalanine residue, for example a D-phenylalanine, or a leucine residue, such as a D-leucine residue.

The substitution of the amino acid residue at position 6 is known from, for example, WO 2016/083531.

—$R^2$

The group —$R^2$, together with the carbonyl group and nitrogen alpha to the carbon to which it is attached, corresponds to the amino acid residue at position 7 in the polymyxin series of compounds.

The group —$R^2$ is $C_{1-4}$ alkyl optionally substituted with one hydroxyl group.

In one embodiment, —$R^2$ is $C_{1-4}$ alkyl. This group is not substituted.

In one embodiment, —$R^2$ is $C_{3-4}$ alkyl, such as $C_4$ alkyl, optionally substituted with one hydroxyl group, such as unsubstituted.

The group amino acid residue at position 7 may the same as the amino acid residue at position 7 of Polymyxin B and Colistin. That is, $R^2$ together with the carbonyl group and nitrogen alpha to the carbon to which it is attached may a L-Leu residue.

In one embodiment, —$R^2$ together with the carbonyl group and nitrogen alpha to the carbon to which it is attached, is a leucine, iso-leucine, phenylalanine, threonine, valine, nor-valine, alanine, threonine or aminobutyrate residue. The amino acid residue may be the L-form.

In one embodiment, —$R^2$ together with the carbonyl group and nitrogen alpha to the carbon to which it is attached, is a leucine, aminobutyrate, or threonine residue. The amino acid residue may be the L-form.

In other embodiments the amino acid residue at position 7 may be substituted with another amino acid residue with respect to Polymyxin B and Colistin.

In one embodiment —$R^2$ together with the carbonyl group and nitrogen alpha to the carbon to which it is attached is a leucine, threonine or aminobutyric acid (Abu) residue, such as L-leucine, L-threonine or L-Abu.

The substitution of the amino acid residue at position 7 is described in, for example, WO 2016/083531 and Velkov et al., amongst others.

—$R^3$

The group —$R^3$, together with the carbonyl group and nitrogen alpha to the carbon to which it is attached, corresponds to the amino acid residue at position 10 in the polymyxin series of compounds.

The group —$R^3$, together with the carbonyl group and nitrogen alpha to the carbon to which it is attached, is threonine, such as L-threonine.

—$R^4$

The group —$R^4$, together with the carbonyl group and nitrogen alpha to the carbon to which it is attached, corresponds to the amino acid residue at position 3 in the polymyxin series of compounds.

In the compounds of the invention, the amino acid residue at position 3 is not L-Dab, which is the amino acid residue at position 3 of Polymyxin B and Colistin. In the compounds of the invention, —$R^4$ together with the carbonyl group and nitrogen alpha to the carbon to which it is attached, is Dap, such as L-Dap.

Compounds where —$R^4$ is a Dap side chain, such as L-Dap, may be prepared using the methods described in WO 2015/135976.

In the compounds of formula (I), the amino group within the Dap side chain may be protected, for example the amino group may be protected with Boc.

—$R^8$

The group —$R^8$, together with the carbonyl group and nitrogen beta to the carbon to which it is attached via a hydroxymethylene spacer (—CH(OH)—), corresponds to the amino acid residue at position 2 in the polymyxin series of compounds.

The amino acid residue at position 2 may the same as the amino acid residue at position 2 of Polymyxin B and Colistin. That is, $R^1$ together with the carbonyl group and nitrogen beta to the carbon to which it is attached via a hydroxymethylene spacer may be a L-Threonine residue.

The amino acid residue including the group —$R^8$ corresponds to position 2 in the polymyxin series of compounds.

In one embodiment, —$R^8$ is methyl. The resulting amino acid is therefore Thr.

In one embodiment, —$R^8$ is H. The resulting amino acid is therefore Ser.

Typically —$R^8$ is methyl.

—X—

The group —X— is —C(O)—*.

The asterisk indicates the point of attachment to NH, the amino terminal of the polymyxin nonapeptide core, such as the amino acid at position 2. The left-hand side of the group —X— is the point of attachment to —$R^{15}$.

—$R^{15}$

The group —$R^{15}$, together with —X—, is a modification of the N terminal of the polymyxin core.

The compounds of the invention contain a stereocentre at the β-position of the γ-aminopropyl group in the N-terminal moiety, —$R^{15}$. It has been found that one of the stereoisomers is associated with lower cytotoxicity and lower kidney drug levels. This stereoisomer is the stereoisomer that elutes more rapidly on reverse phase chromatography, as described in detail in the worked examples of the present case.

In one embodiment, the group —$R^{15}$ is:

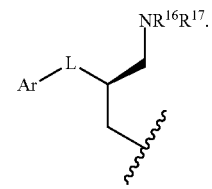

This stereoform is the faster eluting stereoform in the reverse phase chromatography.

Alternatively, the group —$R^{15}$ may be:

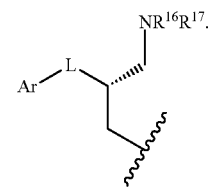

This stereoform is the slower eluting stereoform.

In one embodiment, the group —$R^{15}$ is:

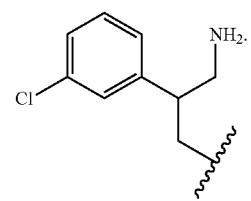

In one embodiment, the group —R$^{15}$ is:

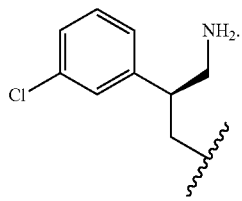 [SMILES: *C[C@H](CN)c1cccc(Cl)c1]

Exemplary groups within —R$^{15}$ are set out below.
—R$^{16}$ and —R$^{17}$

The groups —R$^{16}$ and —R$^{17}$ are both hydrogen.

In the compounds of formula (I), the group —NR$^{16}$R$^{17}$ may be protected, for example the group —NR$^{16}$R$^{17}$ may be Boc-protected.

-L-

The group may be a covalent bond methylene (—CH$_2$—). Typically, -L- is a covalent bond.

—Ar

The group —Ar is an aryl group, such as a carboaryl or heteroaryl group. The aryl group is optionally substituted.

The aryl group may be a C$_6$ aryl group, such as phenyl, or a C$_5$ aryl group, such as thiophene.

The group —Ar may be phenyl, and this is optionally substituted, such as substituted. In one embodiment, —Ar is unsubstituted phenyl.

The aryl group may be substituted, such as with one or more groups —R$^S$. Each group —R$^S$ is independently selected from halo, alkyl, haloalkyl and aryl, such as halo and alkyl.

An aryl group may be substituted with one, two or three —R$^S$ groups, such as one or two groups, such as one group (monosubstituted).

A halo group may be selected from fluoro, chloro, bromo and iodo, and may be selected from fluoro and chloro, such as chloro.

A halo group may be chloro.

An alkyl group may be C$_{1-6}$ alkyl, such as C$_{1-4}$ alkyl, such as C$_{1-3}$ alkyl, such as C$_3$ alkyl. An alkyl group may be selected from methyl, ethyl, and propyl, including n-propyl and i-propyl.

An alkyl group may be i-propyl.

A haloalkyl group may be a C$_{1-6}$ alkyl group, such as C$_{1-4}$ alkyl, such as C$_{1-2}$ alkyl, substituted with one or more halo groups. The alkyl group may be per-substituted with halo, such as per-substituted with fluoro.

A haloalkyl group may be trifluoromethyl.

Where —R$^S$ is an aryl group, this may be carboaryl or heteroaryl. The aryl may be C$_{5-6}$ aryl, such as C$_5$ aryl. A C$_5$ aryl may be selected from thiophenyl, furanyl, pyrrolyl, pyrazolyl, thiazolyl, isothiazolyl, oxazolyl and isoxazolyl. A C$_6$ aryl may be phenyl An aryl group may be thiophenyl, such as thiophen-2-yl.

The aryl group may itself be optionally substituted with one, two or three —R$^{Ar}$ groups, such as one or two groups, such as one group (monosubstituted). Each group —R$^{Ar}$ is independently selected from halo, alkyl, haloalkyl and aryl, such as halo and alkyl. These groups may have the same meanings as the groups described above, except that the aryl group is not substituted.

The group —Ar may be halophenyl or alkylphenyl.

The halophenyl may be selected from 2-halophenyl, such as 2-chlorophenyl, 3-halophenyl, such as 3-chlorophenyl, and 4-halophenyl, such as 4-chlorophenyl.

The alkylphenyl may be selected from 2-alkylphenyl, such as 2-isopropylphenyl, 3-alkylphenyl, such as 3-isopropylphenyl, and 4-alkylphenyl, such as 4-isopropylphenyl The group —Ar may be 2-chlorophenyl or 3-isopropylphenyl.

The group —Ar may be 2-chlorophenyl.

Selected —R$^{15}$ Groups

The group —R$^{15}$ may be selected from the groups below:

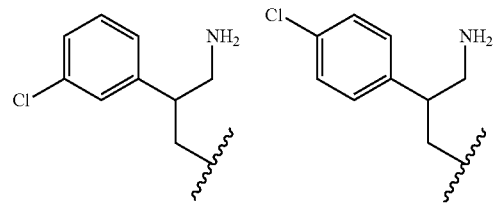

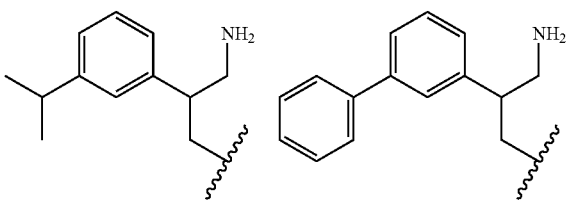

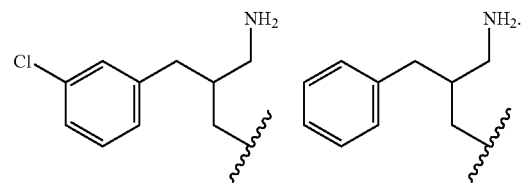

The group —R$^{15}$ may be selected from the groups below:

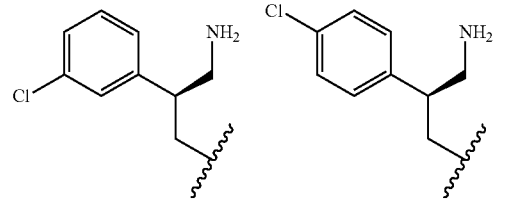

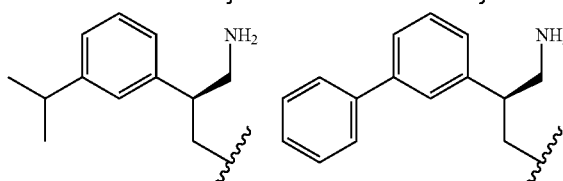

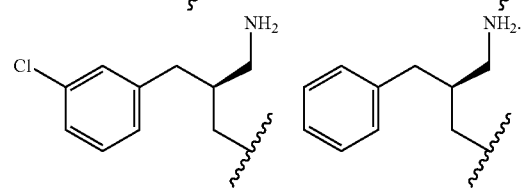

The group —R$^{15}$ may be selected from the groups below:

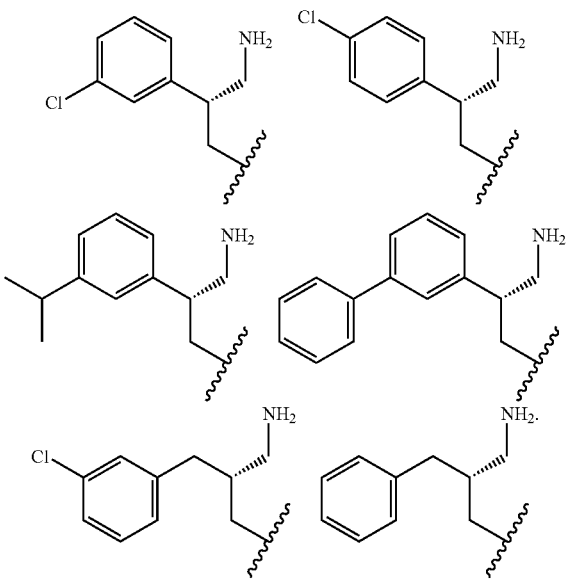

Embodiments Relating to the Compounds of Formula (I)

In some embodiments, the compound of formula (I) is a compound of formula (Ia) having the orientation of R$^1$, R$^2$, R$^3$, and R$^4$ moieties as depicted below:

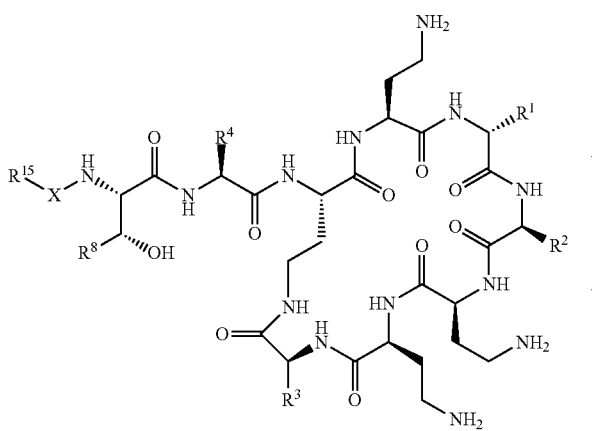

wherein —X—, —R$^1$, —R$^2$, —R$^3$, —R$^4$, —R$^8$ and —R$^{15}$ are as defined for the compounds of formula (I), or a pharmaceutically acceptable salt, solvate, protected form or prodrug form thereof.

Within the compounds of formula (Ia), —R$^1$ together with the carbonyl group and nitrogen alpha to the carbon to which it is attached, is a D-phenylalanine, D-leucine or D-norleucine. Within the compounds of formula (Ia), —R$^2$ together with the carbonyl group and nitrogen alpha to the carbon to which it is attached, is a L-leucine, L-aminobutyrate, or L-threonine residue.

The compounds of formula (Ia) may be compounds where -L- is a covalent bond or —CH$_2$—, and —Ar is phenyl optionally substituted with one or two groups selected from the group consisting of halo, C1-C6 alkyl, optionally substituted aryl and optionally substituted heteroaryl. For example, —Ar may be phenyl optionally substituted with one or two groups selected from the group consisting of chloro, bromo, thiophenyl, phenyl, methyl, isopropyl, and isobutyl.

Here, —Ar may be selected from phenyl, 3-chlorophenyl, 4-chlorophenyl, 3-isopropylphenyl, 3-isobutylphenyl, 3-methylphenyl, 3-bromophenyl, 1,1'-biphenyl-3-yl, 3,5-dichlorophenyl, and thiophen-3-ylphenyl.

The compounds of the present invention may be compounds of formula (I) where:
- —R$^1$, together with the carbonyl group and nitrogen alpha to the carbon to which it is attached, is a D-phenylalanine, D-leucine or D-norleucine;
- —R$^2$, together with the carbonyl group and nitrogen alpha to the carbon to which it is attached, is a L-leucine, L-aminobutyrate, or L-threonine residue;
- —R$^3$ is L-threonine;
- —R$^4$ is L-Dap;
- —R$^8$ is methyl; and
- R$^{15}$—X— is selected from the group consisting of:

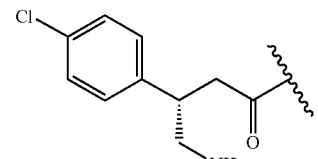
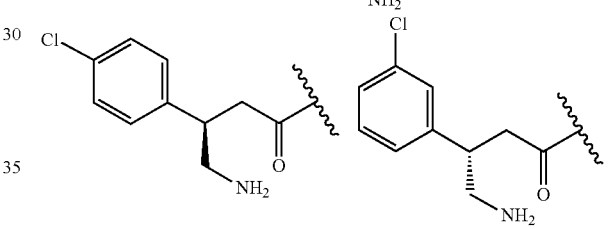
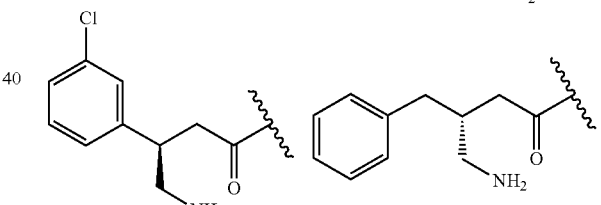
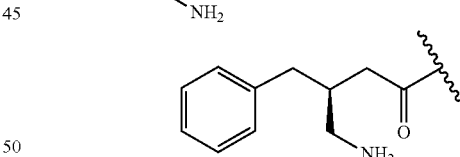
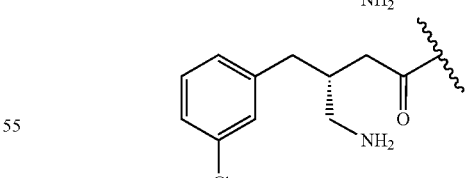
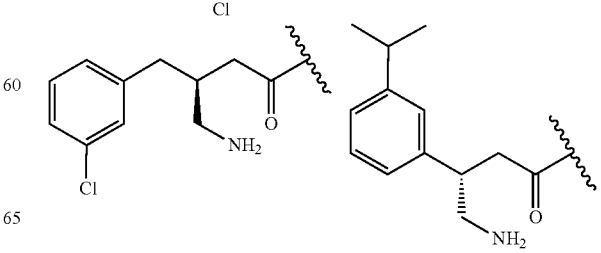

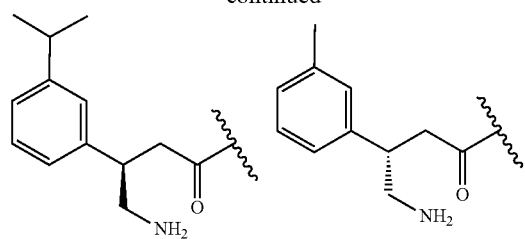
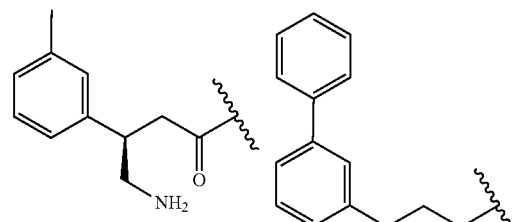
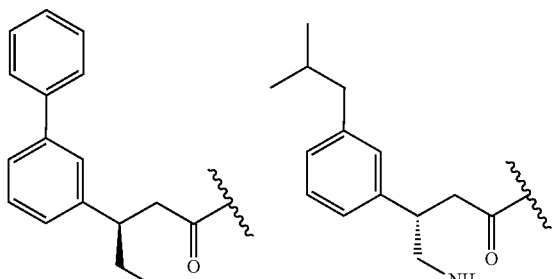
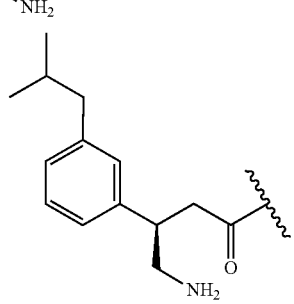
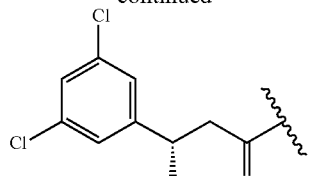
and salts, solvates, protected forms and prodrug forms thereof.
Compound (II) and Compound (III)
The compound of formula (I) may be a compound of formula (II) as shown below:
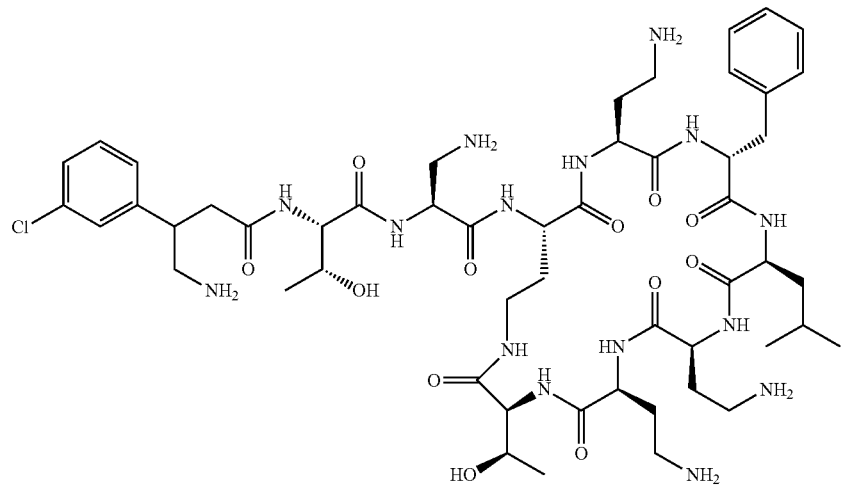 [SMILES: CC(C)C[C@@H]1NC(=O)[C@@H](Cc2ccccc2)NC(=O)[C@H](CCN)NC(=O)[C@@H](NC(=O)[C@H](CN)NC(=O)[C@@H](NC(=O)CC(CN)c2cccc(Cl)c2)[C@@H](C)O)CCNC(=O)[C@H]([C@@H](C)O)NC(=O)[C@H](CCN)NC(=O)[C@H](CCN)NC1=O]
and salts, solvates and protected forms thereof.

The compound of formula (I) may be a compound of formula (IIa) as shown below:
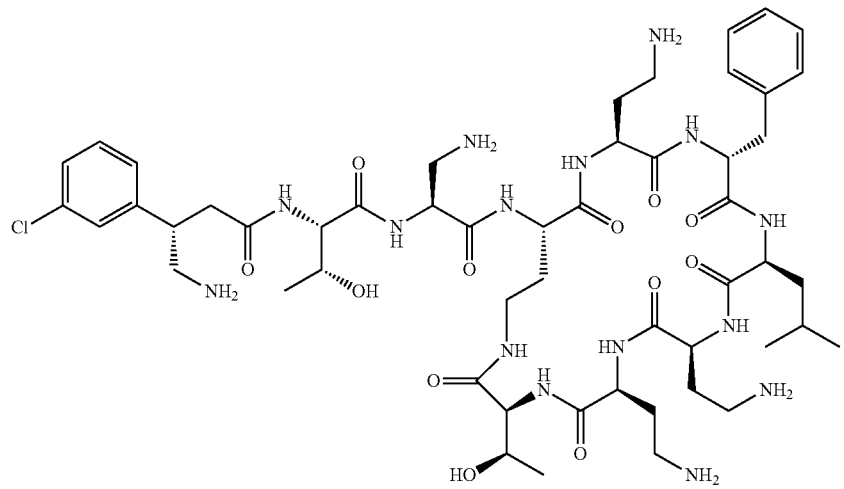
and salts, solvates and protected forms thereof.
The compound of formula (I) may be a compound of formula (IIb) as shown below:
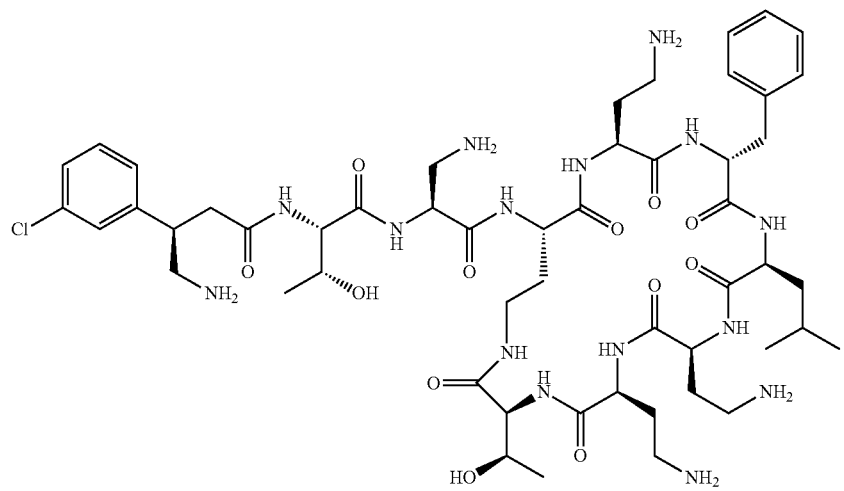 [SMILES: CC(C)C[C@@H]1NC(=O)[C@@H](Cc2ccccc2)NC(=O)[C@H](CCN)NC(=O)[C@@H](NC(=O)[C@H](CN)NC(=O)[C@@H](NC(=O)C[C@@H](CN)c2cccc(Cl)c2)[C@@H](C)O)CCNC(=O)[C@H]([C@@H](C)O)NC(=O)[C@H](CCN)NC(=O)[C@H](CCN)NC1=O]
and salts, solvates and protected forms thereof.

The compound of formula (I) may be a compound of formula (III) as shown below:

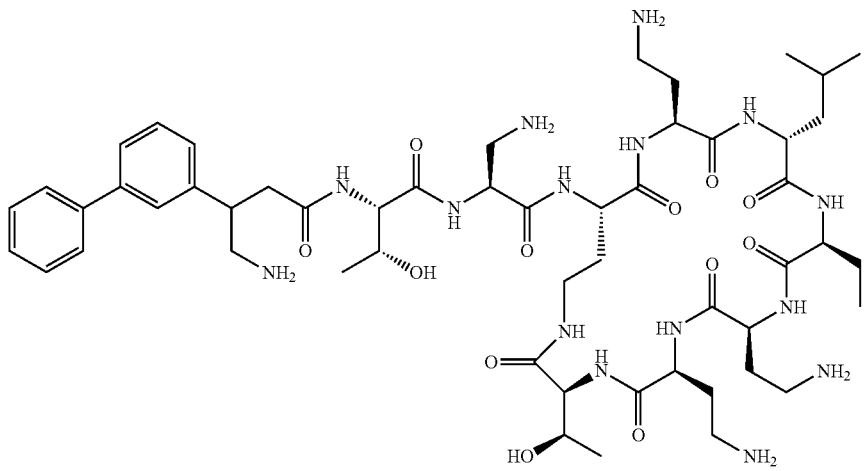 [SMILES: CC[C@@H]1NC(=O)[C@@H](CC(C)C)NC(=O)[C@H](CCN)NC(=O)[C@@H](NC(=O)[C@H](CN)NC(=O)[C@@H](NC(=O)CC(CN)c2cccc(-c3ccccc3)c2)[C@@H](C)O)CCNC(=O)[C@H]([C@@H](C)O)NC(=O)[C@H](CCN)NC(=O)[C@H](CCN)NC1=O]

and salts, solvates and protected forms thereof.

The compound of formula (I) may be a compound of formula (III) as shown below:

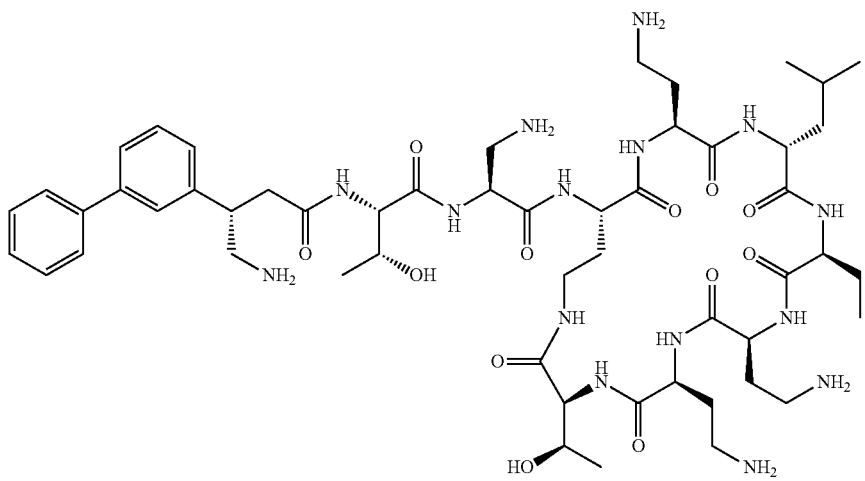 [SMILES: CC[C@@H]1NC(=O)[C@@H](CC(C)C)NC(=O)[C@H](CCN)NC(=O)[C@@H](NC(=O)[C@H](CN)NC(=O)[C@@H](NC(=O)C[C@H](CN)c2cccc(-c3ccccc3)c2)[C@@H](C)O)CCNC(=O)[C@H]([C@@H](C)O)NC(=O)[C@H](CCN)NC(=O)[C@H](CCN)NC1=O]

and salts, solvates and protected forms thereof.

Polymyxin Compounds

The compounds for use in the present case are based on modified forms of known polymyxin compounds, such as Polymyxin B nonapeptide and Colistin nonapeptide Polymyxin B nonapeptide has the structure shown below:

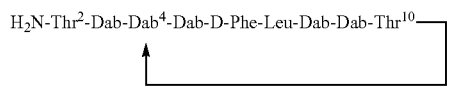

where positions 2, 4 and 10 are indicated (with reference to the numbering system used for the Polymyxin B decapeptide), and the amino acid residues are in the L-configuration, unless indicated.

The compounds of the invention are derivatives of polymyxin B nonapeptide, where (i) the N terminal amino group, —$NH_2$, is replaced with the group —NH—X—$R^{15}$ as described herein; (ii) the amino acid residue at position 3 is substituted with Dap, and optionally (iii) the amino acid residues at 2, 6 and/or 7 are substituted with another amino acid residue.

For convenience, the compounds of the invention are represented by the formula (I) where the amino acids at positions 2, 3, 6, 7 or 10 are determined by the nature of the groups $R^8$, $R^4$, $R^1$, $R^2$ and $R^3$ respectively. Compounds of the invention, which include the variants described above, are biologically active.

Methods of Synthesis

The preparation of the compounds of the invention will be familiar to those of skill in the art, particularly having knowledge of the methods described in WO 2015/135976 for the preparation of modified polymyxin nonapeptides. The methods described in the art may be readily adapted for use in the preparation of the compounds of the present case, taking into account the novel N terminal groups employed in the present case.

Generally, a compound of the invention may be prepared by coupling a suitably protected polymyxin nonapeptide intermediate with a carboxylic acid having the group —$R^{15}$. The product of this reaction is typically the protected form of the compound of formula (I). Removal of the protecting groups may be undertaken as desired. This is the general strategy known from WO 2015/135976.

A suitably protected nonapeptide intermediate may itself be prepared according to the methods set out in in WO 2015/135976. As described herein, a suitably protected nonapeptide intermediate may also be prepared by solid phase synthesis of a linear nonapeptide, followed by cleavage of the linear form from the solid support and then subsequent cyclisation of that linear form between the amino residues at positions 4 and 10.

Compounds of the invention may be made by conventional peptide synthesis, using methods known to those skilled in the art. Suitable methods include solid-phase synthesis such as described by de Visser et al, *J. Peptide Res,* 61, 2003, 298-306, Vaara et al, *Antimicrob. Agents and Chemotherapy,* 52, 2008. 3229-3236, or by Velkov et al. *ACS Chem. Biol.* 9, 2014, 1172. These methods include a suitable protection strategy, and methods for the cyclisation step.

Where required, the compound of formula (I) may be at least partially purified, for example to separate diastereomeric forms of the product.

In a further aspect of the invention there is provided a compound of formula (X):

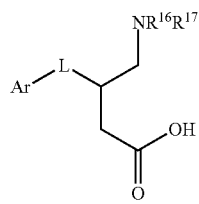

where:
—$R^{16}$ is hydrogen;
—$R^{17}$ is hydrogen
-L- is a covalent bond or methylene;
—Ar is optionally substituted aryl, such as substituted phenyl and salts, solvates, protected forms and activated forms thereof.

The compound of formula (X) finds use in the preparation of the compounds of formula (I). Typically the compound (X), such as in its protected form, is coupled with a protected polymyxin nonapetide of formula (XI) to yield a protected form of the compound of formula The embodiments for the compound of formula (I) in relation to the groups -L- and —Ar also apply to the compounds of formula (X).

Typically, the amino functionality, which is the group —$NR^{16}R^{17}$, is protected. In one embodiment, the amino functionality in the compound of formula (X) is Boc- or CBZ-protected. Here —$R^{16}$ is hydrogen and —$R^{17}$ is —C(O)O-t-Bu or —C(O)O—Bn.

The compound of formula (XI) is a compound of formula (I) except that the group $R^{15}$—X— is hydrogen, and salts, solvates, and protected forms thereof.

The selected embodiments for the compound of formula (I) in relation to the groups —$R^1$, —$R^2$, —$R^3$, —$R^4$ and —$R^8$ also apply to the compounds of formula (XI).

The compound of formula (XI) is typically protected, and more specifically the amino groups in the side chains of the amino acid residues at positions 3, 5, 8 and 9 are protected, for example each of the amino acids at positions 3, 5, 8 and 9 is Boc-protected or CBZ-protected, and the hydroxyl groups in the side chains of the amino acid residues at position 2 and optionally position 10 are protected, for example each of these amino acids is tBu-protected.

The carboxylic acid compound of formula (X) may be coupled with the amino compound of formula (XI) using conventional amide coupling conditions. The compound of formula (X) may be used in activated form, which form may be generated in situ, for reaction with the compound of formula (XI).

The activated form may be generated in situ through the appropriate choice of coupling agents in the amide bond-forming reaction, optionally in the presence of base.

The carboxylic acid of formula (X) may be activated by reaction of a standard activating agent, such as a carbodiimide, such as DIC (N,N'-diisopropylcarbodiimide) or EDCI (water soluble carbodiimide; 1-ethyl-3-(3-dimethylaminopropyl)carbodiimide). The activated form of the acid is an O-acylisourea.

The carboxylic acid may be activated by a hydroxybenzotriazole or a hydroxyazabenzotriazole, such as HOBt (1-hydroxy-benzotriazole) or HOAt (1-hydroxy-7-aza-benzotriazole). The activated form of the acid is an ester.

The ester may be formed via the carbodiimide-activated form, or it may be formed from the carboxylic acid directly, for example using an appropriate reagent, such as HATU, HBTU, PyBOP, PyBROP, or TBTU.

An organic base may be present for the formation of the activated form, such as DIPEA or TEA.

Protected Forms

Compounds of the invention, such as compounds of formula (I), (II) and (III), may be provided in a protected form. Here, reactive functionality, such as amino functionality, may be masked in order to prevent its reaction during a synthesis step. A protecting group is provided to mask the reactive functionality, and this protecting groups may be removed at a later stage of the synthesis to reveal the original reactive functionality.

In one embodiment, the protected form is a compound where amino, hydroxyl, thiol, and/or carboxyl functionality is protected (masked) by a protecting group. In one embodiment, the protected form is a compound where the side chain functionality of the amino acids residues with the compound are protected.

In the compound of formula (I), (II) and (III), the amino acid residues at positions 5, 8 and 9 are Dab residues, and the side chain of the Dab residue includes amino functionality. The amino acid functionality of each Dab residue may be protected with an amino protecting group, as described herein. Similarly, the amino acid residue at position 3 is Dap, and the side chain of this amino acid residue includes amino functionality.

The group —$R^{15}$ contains amino functionality in the form of the group —$R^{16}R^{17}$, for example where each of —$R^{16}$ and —$R^{17}$ is hydrogen. The amino functionality may be protected with amino protecting groups, as described herein.

Protecting groups, such as those for amino acid residues, are well known and well described in the art.

Amino acids having side group protection, optionally together with amino and carboxy protection, are commercially available. Thus, a protected polymyxin compound may be prepared from appropriately protected amino acid starting materials.

Velkov et al. describe the step-wise preparation of polymyxin compounds on the solid-phase using suitably protected amino acid. The use of protected-forms of threonine and Dab is disclosed (see Supplementary Information).

Where a protecting group is used is it is removable under conditions that do not substantially disrupt the structure of the polymyxin core, for example conditions that do not alter the stereochemistry of the amino acid residues.

In one embodiment, the protecting groups are acid-labile, base labile, or are removable under reducing conditions.

Example protecting groups for amino functionality include Boc (tert-butoxycabonyl), Bn (benzyl, Bzl), CbZ (benzyloxycarbonyl, Z), 2-CL-Z (2-chloro), ivDde (1-[4,4-dimethyl-2,6-dioxocylcohex-1-ylidene]-3-methylbutyl), Fmoc (fluorenylmethyloxycarbonyl), $HSO_3$-Fmoc (sulfonylated Fmoc, such as 2-sulfo-Fmoc, as described in e.g. Schechter et al, *J. Med Chem* 2002, 45 (19) 4264), Dde (1-[4,4-dimethyl-2,6-dioxocylcohex-1-ylidene]ethyl), Mmt (4-methoxytrityl), Mtt (4-methyltrityl), Nvoc (6-nitroveratroyloxycarbonyl), Tfa (trifluroacetyl), and Alloc (allyloxycarbonyl).

Example protecting groups for aromatic nitrogen functionality includes Boc, Mtt, Trt and Dnp (dinitrophenyl).

In one embodiment, the protecting group for amino functionality is selected from Boc, ivDde, CbZ, Bn and Fmoc and $HSO_3$-Fmoc.

In one embodiment, the protecting group for amino functionality is Boc, ivDde, Fmoc or CbZ, such as Boc, ivDde or Cbz.

Boc protection may be provided for the amino functionality present in the side chains of the amino acid residues present at positions 5, 8 and 9, and optionally position 3.

Example protecting groups for hydroxyl functionality include Trt (trityl), Bn (benzyl), and tBu (tert-butyl).

In one embodiment, the protecting group for hydroxyl functionality is tBu.

Further example protecting groups include silyl ether protecting groups, such as TMS, TES, TBS, TIPS, TBDMS, and TBDPS. Such protecting groups are removable with TBAF, for example.

Example protecting groups for carboxyl functionality include Bn (benzyl, Bz), tBu (tert-butyl), TMSET (trimethylsilylethyl) and Dmab ({1-[4,4-dimethyl-2,6-dioxocylcohex-1-ylidene]-3-methylbutyl}amino benzyl).

Example protecting groups for aromatic nitrogen functionality, for example where such functionality is present in the group —Ar, includes Boc, Mtt, Trt and Dnp (dinitrophenyl).

In some embodiments, only some types of functionality are protected. For example, only amino groups may be protected, such as amino groups in the side chain of an amino acid residue.

In one embodiment, amino groups and hydroxyl groups are protected.

LogP

A compound of the invention, such as a compound of formula (I), (II) or (III), may have a partition-coefficient, such as expressed as a LogP value, within certain limits. The partition-coefficient may provide an indication of the lipophilicity of the compound.

The inventors have established that compounds having a higher lipophilicity have poorer cytotoxicity. The compounds of the invention typically have LogP values that are associated with lower cytotoxicity, such as the LogP values described below.

A LogP value for a compound may be determined experimentally (for example by partition of the compound between octanol and water), or it may be predicted using standard computational methods.

For example, a reference to LogP may be a reference to ALogP, which may be determined using the methods described by Ghose et al. *J. Phys. Chem. A*, 1998, 102, 3762-3772, the contents of which are hereby incorporated by reference in their entirety. Thus, ALogP is the Ghose/Crippen group-contribution estimate for LogP.

In one embodiment, a compound has a LogP value, such as an ALogP value, of at least −6.5, at least −6.6, at least −6.7, at least −6.8, at least −6.9, at least −7.0, at least −7.5, or at least −8.0.

In one embodiment, a compound has a LogP value, such as an ALogP, value, of at most −6.4, at most −6.3, at most −6.2, at most −6.1, at most −6.0, at most −5.9, or at most −5.8.

In one embodiment, a compound has a LogP value within a range having upper and lower limits appropriately selected from the limits given above, for example within the range −5.8 to −8.0, such as −6.0 to −6.7, such as −6.3 to −6.7. These ranges may be selected when the group —$R^2$ is unsubstituted alkyl.

In another embodiment, the compound has a LogP value within the range −6.7 to −7.4. This range may be selected when the group —$R^2$ is alkyl substituted with one hydroxyl group.

Compounds having LogP values, such as ALogP values, within the limits discussed above are found to have excellent activity against both polymyxin-susceptible and polymyxin-resistant bacterial strains. The compounds may have comparable antimicrobial activity to polymyxin B. Advantageously, such compounds may also have reduced cytotoxicity compared with polymyxin B.

The present inventors have found that a compound having optimal LogP values may be obtained by selecting the —$R^{15}$ group of the present case, together with appropriate choices of amino acid residues at position 6 and/or 7 (such as with appropriate selection of —$R^1$ and/or —$R^2$).

Active Agent

The compounds of formula (I), (II) or (III) may each be used together with a second active agent. The inventors have found that such combinations have greater biological activity than would be expected from the individual activity of both compounds. The compounds of formula (I), (II) or (III) can be used to potentiate the activity of the second active agent. In particular, the compounds of formula (I), (II) or (III) may be used together with a second active agent to enhance the antimicrobial activity of that agent, for example against Gram-negative bacteria.

Without wishing to be bound by theory it is believed that the compounds of formula (I), (II) or (III) act on the outer membrane of a cell e.g. a Gram-negative bacterial cell, to facilitate the uptake of the second active agent into that cell. Thus, agents that are otherwise incapable or poor at crossing the outer membrane may be taken up into a target cell by the action of the compounds of formula (I), (II) or (III).

In one embodiment, the combination of a compound of formula (I), (II) or (III) with the second active agent is active against Gram-negative bacteria. Here, it is not essential that individually either of the compound of formula (I), (II) or (III) or the second active agent have activity against Gram-negative bacteria.

In one embodiment, the second active agent is an agent having a measured MIC value against a particular microorganism, such as a bacterium, that is less than 10, less than 5, or less than 1 micrograms/mL. The microorganism may be a Gram-negative bacteria, such as a Gram-negative bacteria selected from the group consisting of *E. coli, S. enterica, K. pneumoniae, K. oxytoca; E. cloacae, E. aero-*

*genes, E. agglomerans, A. calcoaceticus, A. baumannii; Pseudomonas aeruginosa*, and *Stenotrophomonas maltophila*.

Examples of second active agents that have activity against Gram-negative bacteria include beta-lactams, tetracyclines, aminoglycosides and quinolones.

In one embodiment, the second active agent is an agent having a measured MIC value against a particular microorganism, such as a Gram-negative bacterium, that is more than 4, more than 8, more than 16 or more than 32 micrograms/mL. In this embodiment, the second active agent may be active against Gram-positive bacteria. For example, the second active agent is an agent having a measured MIC value against a particular Gram-positive bacterium that is less than 10, less than 5, or less than 1 micrograms/mL. Here, the compound of formula (I), (II) or (III) acts to facilitate the uptake of the second active agent into the Gram-negative bacterial cell. The second active agent is therefore able to act on a target within the Gram-negative bacterial cell, which target may be the same as the second active agent's target in a Gram-positive bacterial cell.

The Gram-positive bacteria may be selected from the group consisting of *Staphylococcus* and *Streptococcus* bacteria, such as *S. aureus* (including MRSA), *S. epidermis, E. faecalis*, and *E. faecium*.

Examples of second active agents that have activity against Gram-positive bacteria (at the MIC values given above, for example), and moderate activity against Gram-negative bacteria, include rifampicin, novobiocin, macrolides, pleuromutilins. In one embodiment, a compound having moderate activity against Gram-negative bacteria may have a measured MIC value against a Gram-negative bacterium that is less than 32, less than 64, or less than 128 micrograms/mL.

Also suitable for use are agents having activity against Gram-positive bacteria and which are essentially inactive against Gram-negative bacteria. Examples include fusidic acid, oxazolidinines (e.g. linezolid), glycopeptides (e.g. vancomycin), daptomycin and lantibiotics. In one embodiment, a compound having essentially no activity against Gram-negative bacteria may have a measured MIC value against a Gram-negative bacterium that is more than 32, more then 64, more than 128, more than 256 micrograms/mL.

Under normal circumstances such agents are not necessarily suitable for use against Gram-negative bacteria owing to their relatively poor ability to cross the outer membrane of a Gram-negative bacterial cell. As explained above, when used together with a compound of formula (I), (II) or (III), such agents are suitable for use.

In one embodiment, the active agent may be selected from the group consisting of rifampicin (rifampin), rifabutin, rifalazil, rifapentine, rifaximin, aztreonam, oxacillin, novobiocin, fusidic acid, azithromycin, ciprofloxacin, meropenem, tigecycline, minocycline, erythromycin, clarithromycin and mupirocin, and pharmaceutically acceptable salts, solvates and prodrug forms thereof.

The present inventors have found that the polymyxin compounds of formula (I), (II) or (III) may be used together with certain compounds in the rifamycin family to treat microbial infections. The rifamycin family includes isolates rifamycin A, B, C, D, E, S and SV, and synthetically derivatised versions of these compounds, such as rifampicin (rifampin), rifabutin, rifalazil, rifapentine, and rifaximin, and pharmaceutically acceptable salts and solvates thereof.

In one embodiment, the active agent is rifampicin (rifampin) and pharmaceutically acceptable salts, solvates and prodrug forms thereof.

Salts, Solvates and Other Forms

Examples of salts of compound of formula (I), (II) and (III) include all pharmaceutically acceptable salts, such as, without limitation, acid addition salts of strong mineral acids such as HCl and HBr salts and addition salts of strong organic acids such as a methanesulfonic acid salt. Further examples of salts include sulfates and acetates such as acetate itself, trifluoroacetate or trichloroacetate.

In one embodiment the compounds of the present disclosure are provided as a sulfate salt or a trifluoroacetic acid (TFA) salt. In one embodiment the compounds of the present disclosure are provided as acetate salts, such as acetate.

A compound of formula (I), (II) or (III) can also be formulated as a prodrug. Prodrugs can include an antibacterial compound herein described in which one or more amino groups are protected with a group which can be cleaved in vivo, to liberate the biologically active compound. In one embodiment the prodrug is an "amine prodrug". Examples of amine prodrugs include sulphomethyl, as described in e.g., Bergen et al, *Antimicrob. Agents and Chemotherapy*, 2006, 50, 1953 or HSO$_3$-FMOC, as described in e.g. Schechter et al, *J. Med Chem* 2002, 45(19) 4264, and salts thereof. Further examples of amine prodrugs are given by Krise and Oliyai in *Biotechnology: Pharmaceutical Aspects*, 2007, 5(2), 101-131.

In one embodiment a compound of formula (I), (II) or (III) is provided as a prodrug.

A reference to a compound of formula (I), (II) or (III), or any other compound described herein, is also a reference to a solvate of that compound. Examples of solvates include hydrates.

A compound of formula (I), (II) or (III), or any other compound described herein, includes a compound where an atom is replaced by a naturally occurring or non-naturally occurring isotope. In one embodiment the isotope is a stable isotope. Thus a compound described here includes, for example deuterium containing compounds and the like. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{18}$O and $^{18}$O; and the like.

Certain compounds of formula (I), (II) or (III), or any other compound described herein, may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and I-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., $C_{1-6}$ alkyl includes n-propyl and iso-propyl; butyl includes n-, iso-, sec-, and tert-butyl; methoxyphenyl includes ortho-, meta-, and para-methoxyphenyl).

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

One aspect of the present invention pertains to compounds in substantially purified form and/or in a form substantially free from contaminants.

In one embodiment, the substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to an equimolar mixture of enantiomers (i.e., a racemic mixture, a racemate). In one embodiment, the substantially purified form refers to one enantiomer, e.g., optically pure enantiomer.

In one embodiment, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the substantially purified form is at least 60% optically pure (i.e., 60% of the compound, on a molar basis, is the desired stereoisomer or enantiomer, and 40% is the undesired stereoisomer or enantiomer), e.g., at least 70% optically pure, e.g., at least 80% optically pure, e.g., at least 90% optically pure, e.g., at least 95% optically pure, e.g., at least 97% optically pure, e.g., at least 98% optically pure, e.g., at least 99% optically pure.

Methods of Treatment

The compounds of formula (I), (II) or (III), or pharmaceutical formulations containing these compounds, are suitable for use in methods of treatment and prophylaxis. The compounds may be administered to a subject in need thereof. The compounds are suitable for use together with an active agent ("a second active agent"), for example a second active agent that is an antimicrobial agent.

The compounds of formula (I), (II) or (III) are for use in a method of treatment of the human or animal body by therapy. In some aspects of the invention, a compound of formula (I), (II) or (III) may be administered to a mammalian subject, such as a human, in order to treat a microbial infection.

Another aspect of the present invention pertains to use of a compound of formula (I) or (II) in the manufacture of a medicament for use in treatment. In one embodiment, the medicament comprises a compound of formula (I), (II) or (III). In one embodiment, the medicament is for use in the treatment of a microbial infection.

The term "microbial infection" refers to the invasion of the host animal by pathogenic microbes. This includes the excessive growth of microbes that are normally present in or on the body of an animal. More generally, a microbial infection can be any situation in which the presence of a microbial population(s) is damaging to a host animal. Thus, an animal is "suffering" from a microbial infection when excessive numbers of a microbial population are present in or on an animal's body, or when the presence of a microbial population(s) is damaging the cells or other tissue of an animal.

The compounds may be used to treat a subject having a microbial infection, or at risk of infection from a microorganism, such as a bacterium.

The microbial infection may be a bacterial infection such as a Gram-negative bacterial infection.

Examples of Gram-negative bacteria include, but are not limited to, *Escherichia* spp., *Klebsiella* spp., *Enterobacter* spp., *Salmonella* spp., *Citrobacter* spp., and other Enterobacteriaceae, *Pseudomonas* spp., *Acinetobacter* spp., *Stenotrophomonas*, and *Legionella* and numerous others.

Medically relevant Gram-negative bacilli include a multitude of species. Some of them primarily cause respiratory problems (*Haemophilus influenzae, Klebsiella pneumoniae, Legionella pneumophila, Pseudomonas aeruginosa*), primarily urinary problems (*Escherichia coli, Enterobacter cloacae*), and primarily gastrointestinal problems (*Salmonella enterica*).

Gram-negative bacteria associated with nosocomial infections include *Acinetobacter baumannii*, which causes bacteraemia, secondary meningitis, and ventilator-associated pneumonia in intensive-care units of hospital establishments.

In one embodiment the Gram-negative bacterial species is selected from the group consisting of *E. coli, S. enterica, K. pneumoniae, K. oxytoca; E. cloacae, E. aerogenes, E. agglomerans, A. calcoaceticus, A. baumannii; Pseudomonas aeruginosa*, and *Stenotrophomonas maltophila*.

In one embodiment the Gram-negative bacterial species is selected from the group consisting of *E. coli, K. pneumoniae, Pseudomonas aeruginosa*, and *A. baumannii*.

The compounds of formula (I), (II) or (III) or compositions comprising the same are useful for the treatment of skin and soft tissue infections, gastrointestinal infection, urinary tract infection, pneumonia, sepsis, intra-abdominal infection and obstetrical/gynaecological infections. The infections may be Gram-negative bacterial infections.

The compounds of formula (I), (II) or (III) or compositions comprising the same are useful for the treatment of *Pseudomonas* infections including *P. aeruginosa* infection, for example skin and soft tissue infections, gastrointestinal infection, urinary tract infection, pneumonia and sepsis.

The compounds of formula (I), (II) or (III) or compositions comprising the same are useful for the treatment of *Acinetobacter* infections including *A. baumanii* infection, for pneumonia, wound infections, urinary tract infection and sepsis.

The compounds of formula (I), (II) or (III) or compositions comprising the same are useful for the treatment of

*Klebsiella* infections including *K. pneumoniae* infection, for pneumonia, intra-abdominal infection, urinary tract infection, meningitis and sepsis.

The compounds of formula (I), (II) or (III) or compositions comprising the same are useful for the treatment of *E. coli* infection including *E. coli* infections, for bacteraemia, cholecystitis, cholangitis, intra-abdominal infection, urinary tract infection, neonatal meningitis and pneumonia.

The compounds of formula (I), (II), or (III) or compositions comprising the same may be used together with an active agent in methods of treatment.

The active agent may be an agent that has activity against the microorganism. The active agent may be active against Gram-negative bacteria. The active agent may be active against a microorganism selected from the list given above.

In one embodiment, the second active agent has an MIC value of 10 micrograms/mL or less against a microorganism such as *E. coli*, in the absence of the compound of formula (I), (II) or (III). The microorganism may be a microorganism selected from the group above.

Specific compounds for use as second active agents are described herein and include:
- rifampicin, rifabutin, rifalazil, rifapentine, and rifaximin;
- oxacillin, methicillin, ampicillin, cloxacillin, carbenicillin, piperacillin, tricarcillin, flucloxacillin, and nafcillin;
- azithromycin, clarithromycin, erythromycin, telithromycin, cethromycin, and solithromycin;
- aztreonam and BAL30072;
- meropenem, doripenem, imipenem, ertapenem, biapenem, tomopenem, and panipenem;
- tigecycline, omadacycline, eravacycline, doxycycline, and minocycline;
- ciprofloxacin, levofloxacin, moxifloxacin, and delafloxacin;
- Fusidic acid;
- Novobiocin;
- teichoplanin, telavancin, dalbavancin, and oritavancin, and pharmaceutically acceptable salts and solvates thereof;

In one embodiment, specific compounds for use as second active agents are described herein and include rifampicin (rifampin), rifabutin, rifalazil, rifapentine, rifaximin, aztreonam, oxacillin, novobiocin, fusidic acid, azithromycin, ciprofloxacin, meropenem, tigecycline, erythromycin, clarithromycin and mupirocin, and pharmaceutically acceptable salts and solvates thereof.

In an alternative aspect, the compounds of formula (I) are suitable for use in the treatment of fungal infections, for example in combination together with an antifungal agent. The antifungal agent may be selected from a polyene antifungal, for example amphotericin B, an imidazole, triazole, or thiazole antifungal, for example miconazole, fluconazole or abafungin, an allylamine, an echinocandin, or another agent, for example ciclopirox.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviation of symptoms of the condition, amelioration of the condition, and cure of the condition. Treatment as a prophylactic measure (i.e., prophylaxis) is also included. For example, use with patients who have not yet developed the condition, but who are at risk of developing the condition, is encompassed by the term "treatment."

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

The term "treatment" includes combination treatments and therapies, as described herein, in which two or more treatments or therapies are combined, for example, sequentially or simultaneously.

Combination Therapy

A compound of formula (I), (II) or (III) may be administered in conjunction with an active agent. Administration may be simultaneous, separate or sequential.

The methods and manner of administration will depend on the pharmacokinetics of the compound of formula (I), (II) or (III) and the second active agent.

By "simultaneous" administration, it is meant that a compound of formula (I), (II) or (III) and a second active agent are administered to a subject in a single dose by the same route of administration.

By "separate" administration, it is meant that a compound of formula (I), (II) or (III) and a second active agent are administered to a subject by two different routes of administration which occur at the same time. This may occur for example where one agent is administered by infusion and the other is given orally during the course of the infusion.

By "sequential" it is meant that the two agents are administered at different points in time, provided that the activity of the first administered agent is present and ongoing in the subject at the time the second active agent is administered.

Generally, a sequential dose will occur such that the second of the two agents is administered within 48 hours, such as within 24 hours, such as within 12, 6, 4, 2 or 1 hour(s) of the first agent. Alternatively, the active agent may be administered first, followed by the compound of formula (I), (II) or (III).

Ultimately, the order and timing of the administration of the compound and second active agent in the combination treatment will depend upon the pharmacokinetic properties of each.

The amount of the compound of formula (I), (II) or (III) to be administered to a subject will ultimately depend upon the nature of the subject and the disease to be treated. Likewise, the amount of the active agent to be administered to a subject will ultimately depend upon the nature of the subject and the disease to be treated.

Formulations

In one aspect, the present invention provides a pharmaceutical composition comprising a compound of formula (I), (II) or (III) together with a pharmaceutically acceptable carrier. The pharmaceutical composition may additionally comprise a second active agent. In an alternative embodiment, where a second active agent is provided for use in therapy, the second active agent may be separately formulated from the compound of formula (I), (II) or (III). The comments below made in relation to the compound of formula (I), (II) or (III) may therefore also apply to the second active agent, as separately formulated.

While it is possible for the compound of formula (I), (II) or (III) to be administered alone or together with the second active agent, it is desirable to present it as a pharmaceutical formulation (e.g., composition, preparation, medicament) comprising at least one compound of formula (I), (II) or (III), as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one compound of formula (I), (II) or (III), as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound. The composition optionally further comprises the second active agent in a predetermined amount.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, Remington's Pharmaceutical Sciences, 18th edition, Mack Publishing Company, Easton, Pa., 1990; and Handbook of Pharmaceutical Excipients, 5th edition, 2005.

The formulations may be prepared by any methods well known in the art of pharmacy. Such methods include the step of bringing into association the compound of formula (I) or (II) with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or admixed with one or more other pharmaceutically acceptable ingredients. The compound may be presented in a liposome or other microparticulate which is designed to target the compound, for example, to blood components or one or more organs. Where a liposome is used, it is noted that the liposome may contain both the compound of formula (I), (II), (III) and a second active agent.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavoured basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprises a mixture of at least one emulsifier with a fat or an oil or with both a fat and an oil. A hydrophilic emulsifier may be included together with a lipophilic emulsifier which acts as a stabiliser. It is also possible to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound. As an alternative method of administration, a dry powder delivery may be used as an alternative to nebulised aerosols.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichloro-tetrafluoroethane, carbon dioxide, or other suitable gases. Additionally or alternatively, a formulation for pulmonary administration may be formulated for administration from a nebuliser or a dry powder inhaler. For example, the formulation may be provided with carriers or liposomes to provide a suitable particle size to reach the appropriate parts of the lung, to aid delivery of an appropriate does to enhance retention in the lung tissue.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., for example by injection or infusion, intravenously or subcutaneously), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, sugars, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/mL to about 500 µg/mL, for example about 1 ng/mL to about 100 µg/mL, for example from about 10 ng/mL to about 10 µg/mL, for example from about 10 ng/mL to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

Generally, the methods of the invention may comprise administering to a subject an effective amount of a compound of formula (I), (II) or (III) so as to provide an antimicrobial effect. The compound of formula (I), (II) or (III) may be administered at an amount sufficient to potentiate the activity of a second active agent. The second active agent is administered to a subject at an effective amount so as to provide an antimicrobial effect.

It will be appreciated by one of skill in the art that appropriate dosages of the compound of formula (I), (II) or (III) or the active agent, and compositions comprising the compound of formula (I), (II) or (III) or the active agent, can vary from patient to patient. Determining the optimal dosage will generally involve the balancing of the level of therapeutic benefit against any risk or deleterious side effects. The selected dosage level will depend on a variety of factors including, but not limited to, the activity of the particular compound of formula (I), (II) or (III) or the active agent, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound of formula (I), (II) or (III) or the active agent and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of a compound of formula (I), (II) or (III) or the active agent is in the range of about 10 µg to about 250 mg (more typically about 100 µg to about 25 mg) per kilogram body weight of the subject per day. Where the compound of formula (I), (II) or (III) or the active agent is a salt, an ester, an amide, a prodrug, or the like, the amount administered is calculated on the basis of the parent compound and so the actual weight to be used is increased proportionately.

Kits

One aspect of the invention pertains to a kit comprising (a) a compound of formula (I), (II) or (III), or a composition comprising a compound as defined in any one of formula (I), (II) or (III), e.g., typically provided in a suitable container and/or with suitable packaging; and (b) instructions for use, e.g., written instructions on how to administer the compound or composition.

The written instructions may also include a list of indications for which the compound of formula (I), (II) or (III) is a suitable treatment.

In one embodiment, the kit further comprises (c) a second active agent, or a composition comprising the second active agent. Here, the written instructions may also include a list of indications for which the second active agent, together with the compound of formula (I), (II) or (III), is suitable for treatment.

Routes of Administration

A compound of formula (I), (II) or (III), a second active agent, or a pharmaceutical composition comprising the compound of formula (I), (II) or (III), or the second active agent may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection or infusion, including subcutaneous, intradermal, intramuscular, intravenous, intraarterial, intracardiac, intrathecal, intraspinal, intracapsular, subcapsular, intraarticular, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orang-utan, gibbon), or a human. Furthermore, the subject/patient may be any of its forms of development, for example, a foetus.

In one embodiment, the subject/patient is a human.

It is also envisaged that the invention may be practised on a non-human animal having a microbial infection. A non-human mammal may be a rodent. Rodents include rats, mice, guinea pigs, chinchillas and other similarly-sized small rodents used in laboratory research.

Other Options

Each and every compatible combination of the embodiments described above is explicitly disclosed herein, as if each and every combination was individually and explicitly recited.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described. Where technically appropriate embodiments may be combined and thus the disclosure extends to all permutations and combinations of the embodiments provided herein.

Certain aspects and embodiments of the invention will now be illustrated by way of example and with reference to the FIGS. described above.

EXAMPLES

The following examples are provided solely to illustrate the present invention and are not intended to limit the scope of the invention, as described herein.

| Abbreviations | |
|---|---|
| Abbreviation | Meaning |
| PMBN | Polymyxin B nonapeptide |
| PMB | Polymyxin B |
| Thr | Threonine |
| Ser | Serine |
| DSer | D-serine |
| Leu | Leucine |
| Ile | isoleucine |
| Phe | Phenylalanine |
| DPhe | D-phenylalanine |
| Val | Valine |
| Dab | α,γ-Diaminobutyric acid |
| DIPEA | N,N-diisopropylethylamine |
| HATU | 2-(7-aza-1H-benzotriazol-1-yl)-1,1-3,3-tetramethyluronium hexafluorophosphate |
| DCM | Dichloromethane |
| TFA | Trifluoroacetic acid |
| ND | Not determined |

Abbreviations

| Abbreviation | Meaning |
| --- | --- |
| N/A | Not applicable |
| DMF | N,N-Dimethylformamide |
| PMBH | Polymyxin B heptapeptide (3-10) |
| PMBD | Polymyxin B decapepide |
| Pro | Proline |
| Dap | α,β-Diaminopropionic acid |
| Gly | Glycine |
| NorLeu | Norleucine |
| Ruphos | 2-Dicyclohexylphosphino-2',6'-diisopropoxybiphenyl |
| Xphos | 2-Dicyclohexylphosphino-2',4',6'-triisopropylbiphenyl |
| SFC | Supercritical fluid chromatography |
| Fmoc | Fluorenylmethyloxycarbonyl |
| Cbz | Benzyloxycarbonyl |
| HCTU | O-(1H-6-Chlorobenzotriazole-1-yl)-1,1,3,3-tetramethyluronium hexafluorophosphate |
| Boc | tert-Butyloxycarbonyl |
| PyBOP | (Benzotriazol-1-yloxy)tripyrrolidinophosphonium hexafluorophosphate |
| NMM | N-Methyl morpholine |
| THF | Tetrahyrofuran |
| ivDde | 1-(4,4-Dimethyl-2,6-dioxocyclohex-1-ylidene)-3-methylbutyl |
| DPPA | Diphenylphosporyl azide |
| TIS | Tri-isopropyl silane |
| HOBt | 1-Hydroxybenzotriazole |
| IPA | Isopropanol |

Synthesis Examples

Synthesis of N-Terminal Acids

In the present work, 3-substituted 4-aminobutanoic acids were used in suitably protected form. Synthesis of non-standard amino acids are detailed below, together with methodology for enantiomer separation

4-((Tert-Butoxycarbonyl)Amino)-3-(3-Chlorophenyl)Butanoic Acid—Isomer 1 and Isomer 2

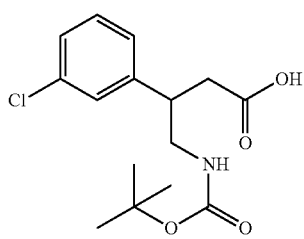 [SMILES: CC(C)(C)OC(=O)NCC(CC(=O)O)c1cccc(Cl)c1]

(i) Methyl 3-(3-Chlorophenyl)-4-Nitrobutanoate

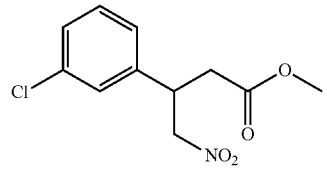 [SMILES: COC(=O)CC(C[N+](=O)[O-])c1cccc(Cl)c1]

A mixture of 3-chlorocinnamic acid (10 g), methanol (100 mL) and concentrated sulfuric acid (4 mL) was stirred at room temperature for 20 h. The mixture was evaporated to dryness and the residues partitioned between dichloromethane (DCM) and water. The aqueous phase was separated and extracted with additional DCM. The organic extracts were combined, dried with magnesium sulfate, filtered and evaporated to dryness, producing the methyl ester as a white solid (10.19 g). This solid was dissolved in nitromethane (32 mL) and treated with 1,8-diazabicyclo[5.4.0]undec-7-ene (DBU) (8.5 mL). The mixture was stirred at room temperature for 20 h, then evaporated to dryness and the residues partitioned between aqueous 0.5 M HCl and diethyl ether. The aqueous phase was separated and extracted with additional diethyl ether. The organic extracts were combined, washed with brine, dried with magnesium sulfate, filtered and evaporated to dryness. The residues were purified on silica, eluting with hexane and ethyl acetate (0-100%). The appropriate fractions were combined and evaporated to dryness, producing the desired product as a yellow oil (9.93 g, 70% yield).

$^1$H NMR (400 MHz, CDCl$_3$): δ (ppm) 2.71-2.79 (2H, m), 3.66(3H, s), 3.93-4.01 (1H, m), 4.62 and 4.73 (2H, ABq, appears as 2×dd, J 12.8, 8.0 Hz), 7.11-7.28 (4H, m).

(ii) Methyl 4-Amino-3-(3-Chlorophenyl)Butanoate

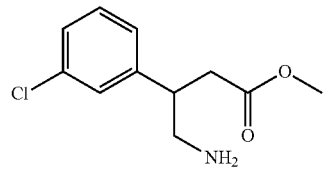

To a solution of methyl 3-(3-chlorophenyl)-4-nitrobutanoate (9.93 g) in acetic acid (90 mL) stirred at ca. 0° C. was added zinc powder (20.1 g) portion-wise (caution: delayed exotherm). The mixture was allowed to warm to room temperature, stirring for 19 h. The mixture was evaporated to dryness and the residues partitioned between aqueous NaHCO$_3$ and ethyl acetate. The mixture was then filtered through Celite and the aqueous and organic phases separated. The aqueous phase was re-extracted with additional ethyl acetate. The organic extracts were combined, washed with brine, dried with magnesium sulfate, filtered and evaporated to dryness, producing the desired product as an orange oil (4.80 g).

(iii) Title Compound—Racemic

A mixture of methyl 4-amino-3-(3-chlorophenyl)butanoate (4.80 g), di-tert-butyl dicarbonate (5.28 g) and dichloromethane (100 mL) was stirred at room temperature for 18 h. The mixture was evaporated to dryness and the residues purified on silica, eluting with petroleum ether 40-60 and ethyl acetate (0-100%). The appropriate fractions were combined and evaporated to dryness, producing the Boc-protected ester methyl 4-((tert-butoxycarbonyl)amino)-3-(3-chlorophenyl)butanoate as a cream solid (2.59 g).

A mixture of methyl 4-((tert-butoxycarbonyl)amino)-3-(3-chlorophenyl)butanoate (2.49 g), lithium hydroxide (546 mg), 1,4-dioxane (40 mL) and water (40 mL) was stirred at room temperature for 64 h. The mixture was then evaporated to dryness. The residues were dissolved in water, neutralised with aqueous 1 M HCl and extracted with ethyl acetate (×2). The organic extracts were combined, washed with brine, dried with magnesium sulfate, filtered and evaporated to dryness, producing the desired product as a yellow oil (2.51 g).

m/z 314 (MH$^+$) $C_{15}H_{20}ClNO_4$ requires 313.11. $^1$H NMR (400 MHz, $CD_3OD$): δ (ppm) 1.40 (9H, s), 2.42-2.73 (2H, m), 3.24-4.49 (4.4 H, m, includes $CH_3OD$, $CH_2$, and CH), 7.17-7.38 (4H, m).

(iv) Title Compound—Separation of Isomers—Method 1

4-((tert-Butoxycarbonyl)amino)-3-(3-chlorophenyl)butanoic acid (2.09 g) was dissolved to 60 mg/mL in methanol, and was then purified by SFC using the conditions described below (preparative separation conditions 1). Combined fractions containing enriched isomer 1 (faster-running) and isomer 2 (slower-running) were combined, concentrated and each repurified individually under the same chromatographic conditions.

Combined fractions of each of isomer 1 and isomer 2 were then evaporated to near dryness using a rotary evaporator, transferred into final vessels with DCM, which was removed under a stream of nitrogen at 40° C. before being stored in a vacuum oven at 40° C. and 5 mbar for 16 hours.

4-((tert-Butoxycarbonyl)amino)-3-(3-chlorophenyl)butanoic acid (isomer 1)

White solid, 883 mg, 95.6% ee. Retention time 2.89 mins on analytical system 1.

4-((tert-Butoxycarbonyl)amino)-3-(3-chlorophenyl)butanoic acid (isomer 2)

White solid, 876 mg, 98.6% ee. Retention time 3.29 mins on analytical system 1.

Preparative Separation conditions 1:
Berger Multigram II SFC
Column Details: Lux A1 (Phenomenex, 21.2 mm×250 mm, 5 μm)
Column Temperature: 40° C.
Flow Rate: 50 mL/min
BPR: 125 BarG
Detector Wavelength: 210 nm
Injection Volume: 300 μL (18 mg)
Isocratic Conditions: 12:88 EtOH: $CO_2$ (0.1% v/v $NH_3$)
Analysis conditions 1:
Waters UPC2
Column Details: Lux C4 (Phenomenex, 4.6 mm×250 mm, 5 μm)
Column Temperature: 40° C.
Flow Rate: 4 mL/min
Detector Wavelength: 210-400 nm
Injection Volume: 1.0 μL
BPR: 125 BarG
Isocratic Conditions: 10:90 EtOH:$CO_2$ (0.1% v/v $NH_3$)
(v) Title Compound—Separation of Isomers—Method 2
4-((tert-Butoxycarbonyl)amino)-3-(3-chlorophenyl)butanoic acid purified by SFC using the conditions described below (preparative separation conditions 2). After separation, the fractions were dried off via rotary evaporator at bath temperature 40° C. to obtain the desired separated enantiomers. The slower-running enantiomer was further purified on the same column eluting with 20% B.

Preparative separation conditions 2:
Instrument: Thar 200 preparative SFC (SFC-10)
Column: ChiralPak AY, 300×50 mm I.D., 10 μm
Mobile phase: A for $CO_2$ and B for IPA
Gradient: B 25%
Flow rate: 200 mL/min
Back pressure: 100 bar
Column temperature: 38° C.
Wavelength: 220 nm
Cycle time: ~4.5 min
Analytical conditions 2:
Instrument: Waters UPC2 analytical SFC (SFC-H)
Column: ChiralPak AY, 150×4.6 mm I.D., 3 μm
Mobile phase: A for $CO_2$ and B for IPA (0.05% DEA)
Gradient: B 5-40%
Flow rate: 2.5 mL/min
Back pressure: 100 bar
Column temperature: 40° C.
Wavelength: 220 nm 4-((tert-butoxycarbonyl)amino)-3-(3-chlorophenyl)butanoic acid (isomer 1). Retention time 2.796 mins. Assigned the (R)-stereochemistry by comparison with isomer (2) below 4-((tert-butoxycarbonyl)amino)-3-(3-chlorophenyl)butanoic acid (isomer 2). Retention time 3.264 mins. Assigned the (S)-stereochemistry by small molecule crystallography of the BOC-deprotected material, as described below.

(vi) Confirmation of Stereochemistry

Trifluoroacetate salt of (S)-4-amino-3-(3-chlorophenyl)butanoic acid

To an ice water cooled solution of 4-(tert-butoxycarbonylamino)-3-(3-chlorophenyl)butanoic acid isomer 2 (Retention time 3.264 mins on analysis method 2) (1.5 g, 4.78 mmol) in dichloromethane (20 ml) was added trifluoroacetic acid (5 mL). After addition, the mixture was stirred at this temperature for 4 hours. The reaction mixture was then concentrated. The crude mixture was dissolved in water (10 mL) and lyophilized to afford the product; TFA salt of (S)-4-amino-3-(3-chlorophenyl)butanoic acid (1.5 g, 95% yield). LC-MS: m/z 214 (M+H)$^+$ (S)-4-Amino-3-(3-chlorophenyl)butanoic acid To a solution of the trifluoroacetic acid salt of (S)-4-amino-3-(3-chlorophenyl)butanoic acid (0.5 g, 1.53 mmol) in water (10 mL), was added diluted aq. ammonium hydroxide until the pH reached 7. The resulting solution was stored on an open 25 mL flask and stood at room temperature for 1 day. Upon crystallization, the mother liquor was decanted, and the solid crystals were submitted to X-ray diffraction studies.

X-ray diffraction studies showed the compound to have the (S) stereochemistry.

X-Ray Diffraction Conditions:

Bruker APEX-II CCD diffractometer was used.

The crystal was kept at 302.71 K during data collection. Using Olex2 (Dolomanov et al.), the structure was solved with the SheIXT [2] structure solution program (Sheldrick A71) using Intrinsic Phasing and refined with the SheIXL [3] refinement package using Least Squares minimisation (Sheldrick C71).

4-((Tert-Butoxycarbonyl)Amino)-3-(2-Chlorophenyl)Butanoic Acid

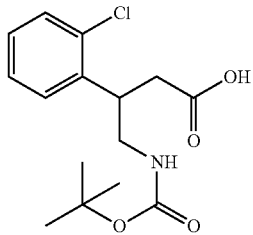 [SMILES: CC(C)(C)OC(=O)NCC(CC(=O)O)c1ccccc1Cl]

The compound was prepared from 2-chlorocinnamic acid following the methodology of 4-((tert-butoxycarbonyl)amino)-3-(3-chlorophenyl)butanoic acid as described in steps (i) to (iii) above. The compound was obtained as a colourless oil.

m/z 314 (MH$^+$), $C_{15}H_2OClNO_4$ exact mass 313.11.

3-Benzyl-4-((Tert-Butoxycarbonyl)Amino)Butanoic Acid

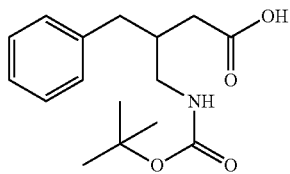 [SMILES: CC(C)(C)OC(=O)NCC(CC(=O)O)Cc1ccccc1]

Methyl 3-benzyl-4-nitrobutanoate (*Tetrahedron Asymmetry*, 19, 2008, 945) was converted to the title compound following the methodology of 4-((tert-butoxycarbonyl)amino)-3-(3-chlorophenyl)butanoic acid as described in steps (i) to (iii) above.

m/z 294 (MH$^+$), $C_{16}H_{23}NO_4$ exact mass 293.16.

4-((Tert-Butoxycarbonyl)Amino)-3-(3-Isobutylphenyl)Butanoic Acid

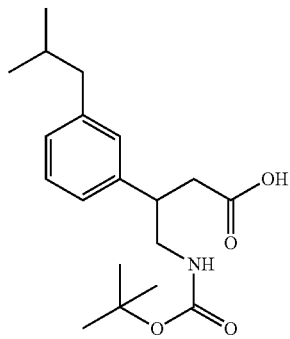 [SMILES: CC(C)Cc1cccc(C(CNC(=O)OC(C)(C)C)CC(=O)O)c1]

(i) Ethyl 3-(3-Bromophenyl)-4-Nitrobutanoate

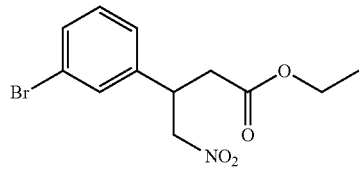

A mixture of sodium hydride (60%) in mineral oil (394.26 mg, 9.86 mmol) and 1,2-dimethoxyethane (22.5 mL) (DME) was cooled to 0° C. Triethylphosphonoacetate (10.2 mL, 51.43 mmol) was added dropwise and the mixture stirred for 10 min. A solution of 3-bromobenzaldehyde (1.0 mL, 8.57 mmol) in DME (5 mL) was added dropwise. The reaction mixture was warmed to room temperature and refluxed for 3 h.

The mixture was evaporated to dryness and the residues partitioned between hexane and water. The aqueous layer was separated and extracted with additional hexane. The organic extracts were combined, washed with water, dried with MgSO$_4$, filtered and evaporated to dryness. The residues were purified on silica eluting with petroleum ether 40-60 and ethyl acetate (0-100%). The appropriate fractions were combined and evaporated to dryness, producing ethyl (E)-3-(3-bromophenyl)prop-2-enoate as a white solid (1.44 g, 65%). This was converted to ethyl 3-(3-bromophenyl)-4-nitrobutanoate using the conditions for nitration in the preparation of 4-((tert-butoxycarbonyl)amino)-3-(3-chlorophenyl)butanoic acid in step (i), as described above, to give the product in 60% yield.

m/z 316, 318 (MH$^+$). $C_{12}H_{14}BrNO_4$ requires 315.01.

(ii) Ethyl 4-Amino-3-(3-Bromophenyl)Butanoate

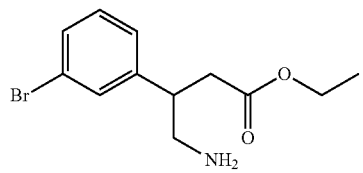 [SMILES: CCOC(=O)CC(C[N+](=O)[O-])c1cccc(Br)c1]

Ethyl 3-(3-bromoophenyl)-4-nitrobutanoate (1.08 g) was converted to ethyl 4-amino-3-(3-bromophenyl)butanoate using the conditions described above for 4-((tert-butoxycarbonyl)amino)-3-(3-chlorophenyl)butanoic acid in step (ii), to give the product in 67% yield.

m/z 286 and 288 (MH$^+$), $C_{12}H_{16}BrNO_2$ exact mass 285.04.

(iii) Ethyl 4-((Tert-Butoxycarbonyhamino)-3-(3-Bromophenyl)Butanoate

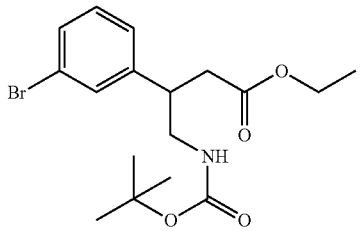 [SMILES: CCOC(=O)CC(CNC(=O)OC(C)(C)C)c1cccc(Br)c1]

Ethyl 4-amino-3-(3-bromophenyl)butanoate (655 mg) was converted to ethyl 4-((tert-butoxycarbonyl)amino)-3-(3-bromophenyl)butanoate under the conditions described above for 4-((tert-butoxycarbonyl)amino)-3-(3-chlorophenyl)butanoic acid in step (iii), to give the product in 72% yield.

m/z 386 and 388 (MH$^+$), C$_{17}$H$_{24}$BrNO$_4$ exact mass 385.09.

(iv) Ethyl 4-((Tert-Butoxycarbonyl)Amino)-3-(3-Isobutylphenyl)Butanoate

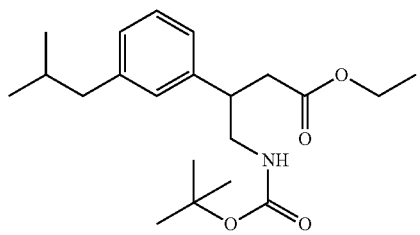 [SMILES: CCOC(=O)CC(CNC(=O)OC(C)(C)C)c1cccc(CC(C)C)c1]

A mixture of Ruphos (48.3 mg, 0.1 mmol), potassium phosphate tribasic (330 mg, 1.55 mmol), ethyl 3-(3-bromophenyl)-4-(tert-butoxycarbonylamino)butanoate (200 mg, 0.52 mmol) and isobutylboronic acid (132 mg, 1.29 mmol) in toluene (9 mL) was degassed four times by evacuation/nitrogen flushing before adding palladium (II) acetate (5.8 mg, 0.03 mmol). The mixture was stirred at 110° C. for 100 min. The reaction mixture was allowed to cool before it was filtered through Celite and left overnight in solution. The mixture was evaporated to dryness and purified on silica, eluting with petroleum ether 40-60 and ethyl acetate (0-100%). The appropriate fractions were combined and evaporated to dryness, producing ethyl 4-((tert-butoxycarbonyhamino)-3-(3-isobutylphenyl)butanoate as a colourless oil, (74 mg, 39%).

m/z 364 (MH$^+$). C$_{21}$H$_{33}$NO$_4$ exact mass 363.24.

(v) Title Compound

A mixture of ethyl 4-(tert-butoxycarbonylamino)-3-(3-isobutylphenyl)butanoate (74 mg, 0.2 mmol) and lithium hydroxide (15 mg, 0.6 mmol) in 1,4-dioxane (3 mL) and water (3 mL) was stirred at room temperature for 16 h. The mixture was evaporated to dryness and the residues partitioned between ethyl acetate and water. The organic phase was separated and discarded. The aqueous was acidified with 1M HCl(aq) and extracted with ethyl acetate (×2). The organic extracts were combined, dried with MgSO$_4$, filtered and evaporated to dryness, producing 4-((tert-butoxycarbonyl)amino)-3-(3-isobutylphenyl)butanoic acid as a colourless oil (65 mg). m/z 336 (MH$^+$) C$_{19}$H$_{29}$NO$_4$ exact mass 335.21.

4-((Tert-Butoxycarbonyl)Amino)-3-(3-Chlorobenzyl)Butanoic Acid

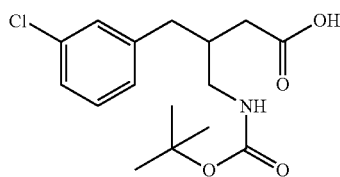 [SMILES: CC(C)(C)OC(=O)NCC(CC(=O)O)Cc1cccc(Cl)c1]

2-(3-Chlorophenyl) acetaldehyde was converted to ethyl 3-(3-chlorobenzyl)-4-nitrobutanoate as described for 4-((tert-butoxycarbonyhamino)-3-(3-isobutylphenyl)butanoic acid in step (i), as described above. Reduction and protection as in step (ii) and (iii), followed by hydrolysis as in step (v) above afforded the title compound as a colourless oil.

m/z 328 (MH$^+$). C$_{16}$H$_{22}$ClNO$_4$ exact mass 327.12.

4-(((Benzyloxy)Carbonyl)Amino)-3-(3-Isopropylphenyl)Butanoic Acid

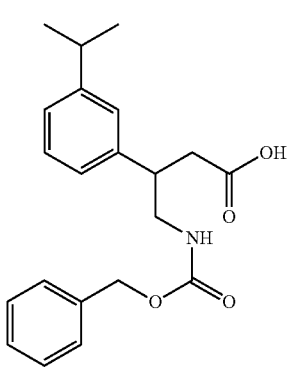 [SMILES: CC(C)c1cccc(C(CNC(=O)OCc2ccccc2)CC(=O)O)c1]

A mixture of ethyl 4-amino-3-(3-isopropylphenyl)butanoate (1.55 g, 6.21 mmol) (prepared using the methodology of 4-((tert-butoxycarbonyl)amino)-3-(3-isobutylphenyl)butanoic acid steps (i) through (ii), as described above), and sodium bicarbonate (0.783 g 9.32 mmol) was dissolved in water (10 mL) and 1,4-dioxane (5 mL). The mixture was cooled in an ice bath, and treated with a solution of benzyl chloroformate (0.98 mL, 6.84 mmol). The mixture was stirred at 10° C. for 1 h, then allowed to warm to room temperature. After stirring for 20 h, the mixture was evaporated to dryness, and the residues partitioned between diethyl ether and aqueous 0.5 M HCl. The aqueous layer was separated and extracted with additional diethyl ether. The organic extracts were combined, washed with brine, dried over anhydrous MgSO$_4$, and evaporated. The crude product was purified on silica, eluting with pet ether 40-60 and ethyl acetate (0-100%). Product-containing fractions were combined and evaporated to a pale yellow oil (1.74 g, 73%). The ethyl ester was hydrolysed with lithium hydroxide as previously described in step (iii) for the preparation of 4-((tert-butoxycarbonyl)amino)-3-(3-isobutylphenyl)butanoic acid, followed by chromatography on silica eluting with petroleum ether 40-60 and ethyl acetate (0-100%) to afford the title compound as a white solid (60%).

m/z 356 (MH$^+$). C$_{21}$H$_{25}$NO$_4$ exact mass: 355.18.

4-([1,1'-Biphenyl]-3-yl)-3-(((Tert-Butoxycarbonyl)Amino)Methyl)Butanoic Acid

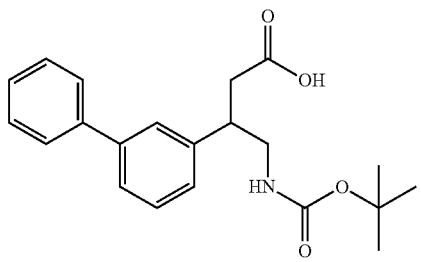 [SMILES: CC(C)(C)OC(=O)NCC(CC(=O)O)c1cccc(-c2ccccc2)c1]

(i) 4-Amino-3-(3-Bromophenyl)Butanoic Acid Hydrochloride

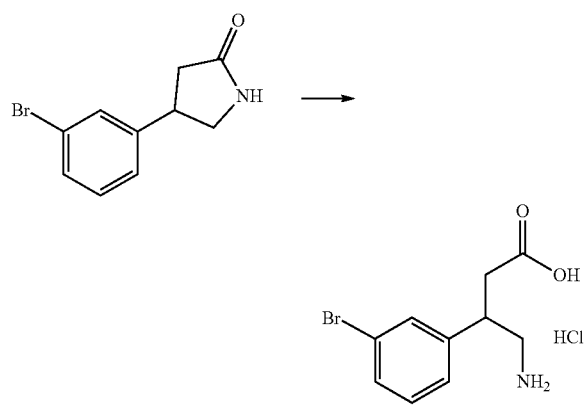

A mixture of 4-(3-bromophenyl)pyrrolidin-2-one (1.0 g, 4.16 mmol) and aqueous 6 M HCl (15.0 mL, 90 mmol) was heated at 100° C. for 16 h. The mixture was evaporated to dryness, co-evaporated with water, followed by ethyl acetate and then dichloromethane (DCM), producing the desired product as a white solid, in an assumed quantitative yield.

m/z 258 and 260 (MH$^+$) C$_{10}$H$_{12}$BrNO$_2$ exact mass: 257.01.

(ii) 3-(3-Bromophenyl)-4-(Tert-Butoxycarbonylamino)Butanoic Acid

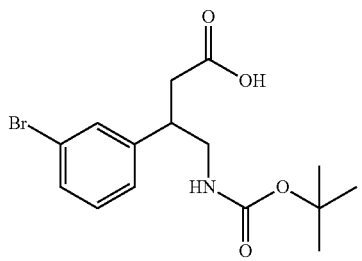 [SMILES: CC(C)(C)OC(=O)NCC(CC(=O)O)c1cccc(Br)c1]

A mixture of 4-amino-3-(3-bromophenyl)butanoic acid hydrochloride (1.31 g, 4.45 mmol), tert-butoxycarbonyl tert-butyl carbonate (Boc-O-Boc, 1.41 g, 6.45 mmol), 1,4-dioxane (8 mL) and aqueous 1 M NaOH (8.0 mL, 8 mmol) was stirred at room temperature for 64 h. The mixture was evaporated to dryness. The residues were dissolved in water, neutralised with aqueous 1 M HCl and extracted with ethyl acetate (×2). The organic extracts were combined, dried with MgSO$_4$, filtered and evaporated to dryness, producing the desired product (1.60 g, 86%) as a colourless oil.

m/z 357.5 and 359.4 (MH$^+$). C$_{15}$H$_{20}$BrNO$_4$ exact mass: 357.06.

(iii) Title Compound

A mixture of 3-(3-bromophenyl)-4-(tert-butoxycarbonylamino)butanoic acid (2.69 g, 7.51 mmol), phenylboronic acid (2.3 g, 18.8 mmol), palladium (II) acetate (84 mg, 0.38 mmol), Xphos (716 mg, 1.5 mmol) and potassium phosphate tribasic (4781.9 mg, 22.53 mmol) in 1,4-dioxane (130 mL) was stirred at 100° C. under an atmosphere of nitrogen for 2 h. The mixture was then allowed to cool to room temperature, filtered through Celite, washed with ethyl acetate and evaporated to dryness. The residues were purified on silica, eluting with petroleum ether and ethyl acetate (0-100%). The appropriate fractions were combined and evaporated to dryness, producing the desired product, 1.44 g, as a grey solid (42% yield).

m/z 355 (M$^+$), seen. C$_{21}$H$_{25}$NO$_4$ exact Mass: 355.18.

(iv) Chiral Separation 4-([1,1'-biphenyl]-3-yl)-3-(((tert-butoxycarbonyl)amino)methyl)butanoic acid (1.44 g) was dissolved to 30 mg/mL in MeOH and was then purified by SFC, using the method below. Combined fractions of each of isomer 1 (faster-running) and isomer 2 (slower-running) were then evaporated to near dryness using a rotary evaporator, transferred into final vessels with DCM, which was removed under a stream of compressed air at 40° C. before being stored in a vacuum oven at 40° C. and 5 mbar until constant weight.

4-([1,1'-biphenyl]-3-yl)-3-(((tert-butoxycarbonyl)amino)methyl)butanoic acid isomer 1. White solid 523 mg. Retention time: (analysis conditions 3) 2.70 min. ee 99.8%.

4-([1,1'-biphenyl]-3-yl)-3-(((tert-butoxycarbonyl)amino)methyl)butanoic acid isomer 2. White solid 537 mg. Retention time: (analysis conditions 3) 3.46 min. ee 99.8%.

Purification conditions 3:

Berger Multigram II SFC

Column Details: Lux A1 (Phenomenex, 21.2 mm×250 mm, 5 µm)

Column Temperature: 40° C.

Flow Rate: 50 mL/min

BPR: 100 BarG

Detector Wavelength: 215 nm

Injection Volume: 1,000 µL (30 mg)

Isocratic Conditions: 15:85 EtOH:CO$_2$ (0.2% v/v NH$_3$)

Analysis conditions 3:

Waters UPC2

Column Details:Amy-C (YMC Gmbh, 4.6 mm×250 mm, 5 µm)

Column Temperature: 40° C.

Flow Rate: 4 mL/min

Detector Wavelength: 210-400 nm
Injection Volume: 1.0 μL
BPR: 125 BarG
Isocratic Conditions: 15:85 EtOH:$CO_2$ (0.2% v/v $NH_3$)

4-((Tert-Butoxycarbonyl)Amino)-3-(3-Methylphenyl)Butanoic Acid

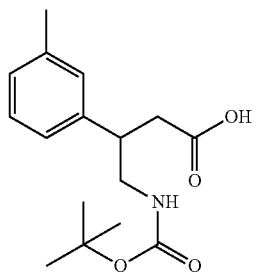 [SMILES: Cc1cccc(C(CNC(=O)OC(C)(C)C)CC(=O)O)c1]

4-(3-Methylphenyl)pyrrolidin-2-one was converted into the title compound using the methodology described above for the preparation of 4-([1,1'-biphenyl]-3-yl)-3-(((tert-butoxycarbonyl)amino)methyl)butanoic acid in steps (i) through (ii). The title compound was obtained as a colourless oil.

m/z 294 ($MH^+$). $C_{16}H_{23}NO_4$ exact mass 293.16.

4-((Tert-Butoxycarbonyl)Amino)-3-(3,5-Dichlorophenyl)Butanoic Acid

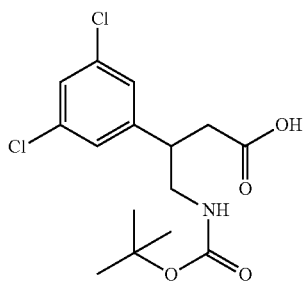 [SMILES: CC(C)(C)OC(=O)NCC(CC(=O)O)c1cc(Cl)cc(Cl)c1]

3,5-Dichlorobenzaldehyde was converted to the title compound using the methodology described above for the preparation of 4-((tert-butoxycarbonyl)amino)-3-(3-isobutylphenyl)butanoic acid in steps (i) through (iii). The ethyl ester was hydrolysed as described for step (v) in the preparation of (3-isobutylphenyl)butanoic acid, to afford the title compound as a colourless oil.

m/z 348. ($MH^+$). $C_{15}H_{19}Cl_2NO_4$ exact mass 347.07.

4-((Tert-Butoxycarbonyl)Amino)-3-(3-(Thiophen-3-yl)Phenyl)Butanoic Acid

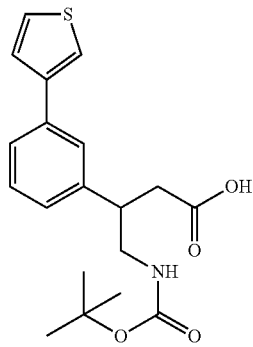 [SMILES: CC(C)(C)OC(=O)NCC(CC(=O)O)c1cccc(-c2ccsc2)c1]

Ethyl 4-((tert-butoxycarbonyl)amino)-3-(3-bromophenyl)butanoate (207 mg, 0.54 mmol) was reacted with 3-thienylboronic acid using the methodology described above for the preparation of (3-isobutylphenyl)butanoic acid in step (iv). The product was hydrolysed as described in step (v) to afford the title compound as a colourless oil.

m/z 362 ($MH^+$). $C_{19}H_{23}NO_4S$ exact mass 361.13.

Intermediate Polymyxin Nonapeptides and Product Compounds

Intermediate 1: H-Thr(O-tBu)-Dap(BOC)-Cyclo[Dab-Dab(BOC)-DPhe-Leu-Dab(BOC)-Dab(BOC)-Thr]

Previously described in WO 2015/135976 as Intermediate 11—Tetra-(N-Boc)-L-Thr(O-tBu)-L-Dap-Polymyxin B heptapeptide.

Intermediate 2: H-Thr(O-$^t$Bu)-Dap(BOC)-Cyclo[Dab-Dab(BOC)-Leu-Leu-Dab(BOC)-Dab(BOC)-Thr]

Previously described in WO 2015/135976 as Intermediate 14—Tetra-(N-Boc)-L-Thr(O-tBu)-L-Dap-Polymyxin E heptapeptide.

Intermediate 3: H-Thr(O-$^t$Bu)-Dap(BOC)-Cyclo[Dab-Dab(BOC)-Dleu-L-Abu-Dab(BOC)-Dab(BOC)-Thr(O-tBu)]

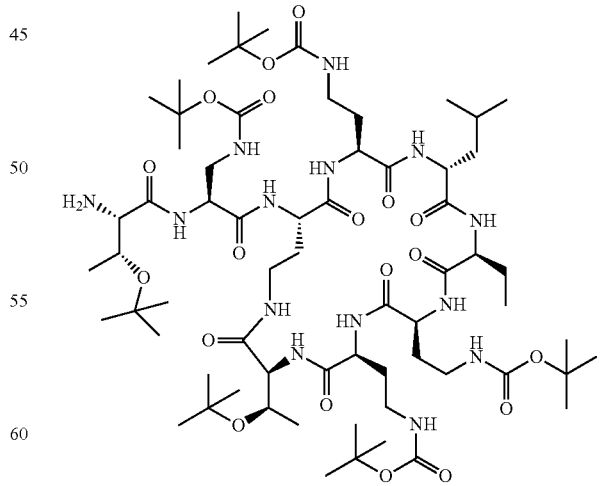

(i) CBZ-Thr(O-$^t$Bu)-Dap(Boc)-Dab-Dab(Boc)-Dleu-L-Abu-Dab(Boc)-Dab(Boc)-Thr(O-tBu)-OH The linear peptide CBZ-Thr(O-tBu)-Dap(Boc)-Dab(ivDde)-Dab(Boc)-Dleu-L-Abu-Dab(Boc)-Dab(Boc)-Thr (O-tBu) was prepared on resin by solid phase peptide synthesis using Fmoc chemistry, using the methodology of General method 3 described above. The sequence commenced with chlorotrityl chloride (CTC)-resin (2.0 g), pre-loaded with Fmoc-Thr(tBu)-OH at a loading of 0.75 mmol/g. Resin-bound peptide (3.93 g, corresponding to 1.5 mmol) was placed in a 500 mL conical flask and treated with 4% hydrazine in DMF (100 mL). The mixture was placed on a shaker and shaken gently for 30 mins. The mixture was poured into a sintered column, then washed with DMF (3×100 mL). Compressed air was applied to remove last traces of DMF. The procedure was then repeated with THF and with DCM.

The resin was then treated with 4:1 DCM: hexafluoroisopropanol (100 mL) to cleave the peptide from the resin. After 30 min the column was drained and the procedure repeated. The resin was then washed three times with DCM (100 mL). The combined eluants and washings were evaporated under reduced pressure and dried in vacuo overnight. Obtained 724 mg white solid (2.35 g, quant.).

m/z 1552, $C_{73}H_{126}N_{14}O_{22}$ requires 1550.92.

(ii) CBZ-Thr(O-tBu)-Dap(Boc)-cyclo[Dab-Dab(Boc)-DLeu-L-Abu-Dab(Boc)-Dab(Boc)-Thr(O-tBu)]

Crude CBZ-Thr(O-tBu)-Dap(Boc)-Dab-Dab(Boc)-DLeu-L-Abu-Dab(Boc)-Dab(Boc)-Thr(O-tBu)-OH (724 mg, 0.466 mmol) was dissolved in DMF (75 mL), treated with diisopropylethylamine (DIPEA) (361 mg 0.49 mL, 2.8 mmol) then cooled in an ice bath. Diphenyl phosphoryl azide (256 mg, 0.2 mL, 0.93 mmol) was added dropwise, then the mixture stirred for 2 h. with ice bath cooling. The ice bath was removed and the solution stirred at room temperature for a further 2 h. The solvent was evaporated and the residue applied to a $SiO_2$ ISCO column (40 g) and chromatographed with 0-10% MeOH in DCM. Product-containing fractions were combined and evaporated to a white foam. Obtained 418 mg (58%).

m/z 1534, $C_{73}H_{124}N_{14}O_{21}$ requires 1532.91.

(iii) Title Compound

CBZ-Thr(O-tBu)-Dap(Boc)-cyclo[Dab-Dab(Boc)-DLeu-L-Abu-Dab(Boc)-Dab(Boc)-Thr(O-tBu)] (531 mg, 0.346 mmol) was dissolved in methanol (50 mL) and treated with ammonium formate (545 mg, 8.6 mmol) and 10% Pd/C (173 mg). After stirring at room temperature overnight, the reaction mixture was filtered through Celite, and the residue washed with MeOH. The solvent was evaporated and the residue dissolved in EtOAc, containing 10% MeOH, washed with water×3 and dried with magnesium sulfate. The solvent was evaporated to leave a white solid. To remove any traces of formate, the solid was dissolved in methanol (160 mL) and shaken with Ambersep 900 resin (12 mL) in for 30 minutes. The mixture was filtered and evaporated to dryness, to obtain 464 mg of white solid (96%).

m/z 1400, $C_{65}H_{118}N_{14}O_{19}$ requires 1398.87.

General Methods

The total synthesis of the polymyxin nonapeptide derivatives was carried out as follows.

A linear peptide with orthogonal protection of the γ-amino group of the Dab residue involved in cyclisation was constructed on-resin, with the C-terminal amino acid (typically Thr) attached to the solid phase. After partial deprotection of the Dab involved in cyclisation (residue 4 in the Polymyxin numbering system), followed by removal from resin, the resulting linear peptides were cyclised off-resin. Two general methods were used, as described below.

General Method 1: Total Synthesis Using CBZ Protection of Amine Groups

Synthesis of the protected linear peptide (residues 2-10 and N-terminal group) was carried out on an automated peptide synthesizer using standard Fmoc solid phase peptide chemistry. Specifically, synthesis was undertaken using Fmoc-Thr(tBu)-PEG-PS resin as starting material. Coupling of the Fmoc-amino acids with CBZ protection on the terminal amino groups was performed using 5 molar equivalents (relative to resin loading) of Fmoc amino acid and HATU in DMF with activation in situ, using 10 molar equivalents of DIPEA. Fmoc deprotection was performed using 20% piperidine in dimethylformamide. BOC was used as the orthogonal protecting group on the Dab involved in cyclisation.

The resin-bound linear peptide was treated with TFA/TIS/$H_2O$ (96/2/2v/v) for 2 h. to reveal the Dab residue involved in cyclisation, and to cleave the peptide from the resin. This material was cyclised using PyBop/HOBt/NMM (4/4/8 molar equivalents relative to the initial loading) in DMF for 3 h. The crude material was partially evaporated, taken up acetonitrile/water and lyophilised overnight. The CBZ groups were then removed using 10% Pd/C in Acetic acid/MeOH/water (5/4/1 v/v).

The crude product was purified and the diastereomers separated by preparative HPLC (Table 3). Note that the specific conditions were optimised for each pair of diastereomers.

General Method 2: Total Synthesis Using Boc Protection of Amine Groups

Synthesis of the protected linear peptide (residues 2-10 and N-terminal group) was carried out on an automated peptide synthesizer using standard Fmoc solid phase peptide chemistry. Specifically, synthesis was undertaken using chlorotrityl chloride (CTC)-resin, pre-loaded with Fmoc-Thr(tBu)-OH (loading ~0.78 mmol/g), on 0.05-0.1 mmol scale. Coupling of the Fmoc-amino acids was performed using 5 molar equivalents (relative to resin loading) of Fmoc amino acid and HATU in DMF with activation in situ, using 10 molar equivalents of DIPEA. Fmoc deprotection was performed using 20% piperidine in dimethylformamide. The ivDde protecting group was used as orthogonal protection on the Dab residue involved in cyclisation.

To remove the ivDde group, the linear peptide was treated with 3% hydrazine in DMF (100 mL per 100 µmol, repeated twice) followed by washing with DMF×3, EtOH×3 and diethyl ether×3. The partially deprotected linear peptide was then cleaved from the resin by washing the resin with 20% HFIP in DCM. The resulting residue was dissolved in 50% acetonitrile/water and freeze dried overnight. The protected linear peptide was dissolved in DMF (20 mL/mmol resin) cyclised with DPPA, (3 molar equivalents relative to the loading of the resin) and DIPEA (6 molar equivalents relative to the loading of the resin). This solution was stirred at room temperature overnight. The BOC groups were removed with TFA, and the crude peptide lyophilised.

The crude product was purified and the diastereomers separated by preparative HPLC using the preparative HPLC conditions 4 described below. Note that the specific conditions were optimised for each pair of diastereomers.

General Method 3: Coupling of Acid to Nonapeptide and Separation

Methods for coupling the N terminal of a nonapeptide to an amino acid are described below in relation to example compounds 5 and 6. The conditions described are adaptable for other combinations of nonapeptide and amino acid.

Step 1

H-Thr(O-$^t$Bu)-Dap(BOC)-Cyclo[Dab-Dab(BOC)-DPhe-Leu-Dab(BOC)-Dab(BOC)-Thr]. (Intermediate 1) (0.07 mmol) was dissolved in dichloromethane (4 mL), and treated with 4-((tert-butoxycarbonyl)amino)-3-(3-chlorophenyl)butanoic acid (1.5 equiv with respect to the polymyxin substrate), N,N-diisopropylethylamine (3.0 equiv.), followed by HATU (2.0 equivalent). After 16 h. the completion of the reaction was confirmed by LCMS and the reaction mixture was evaporated to dryness. Water (approx. 10 mL) was added and the mixture triturated then stirred vigorously for 1 h. The resultant precipitate was collected by filtration and dried in vacuo overnight.

Step 2

The Boc-protected derivative from Step 1 was dissolved in dichloromethane (3 mL) and treated with TFA (1 mL). The reaction mixture was stirred at room temperature until LCMS confirmed complete deprotection. The solvent was evaporated and the residue chromatoghed by preparative HPLC using the conditions given Preparative HPLC conditions 4 to separate the diastereomers. Fractions containing the early-running diastereomer were combined, evaporated to low volume, and lyophilised to afford Example 5 as the TFA salt. Fractions containing the later-running diastereomer were combined, evaporated to low volume, and lyophilised to afford Example 6 as the TFA salt.

Note that the specific conditions were optimised for each pair of diastereomers.

Preparative HPLC conditions 4:
Column: Waters Sunfire C18 OBD 5 μm×19 mm×150 mm
Mobile phase: A: water/acetonitrile 90/10, v/v, 0.15% TFA.
B: acetonitrile/water 90/10, v/v, 0.15% TFA
Flow rate: 10 mL/min

| Gradient: | |
|---|---|
| Time (mins) | % mobile phase A |
| 0 | 100% |
| 3 | 100% |
| 8 | 85% |
| 13.5 | 85% |
| 15 | 75% |
| 18 | 0% |
| 23 | 100% |
| 25 | 100% |
| Detection: | 210 nm |

Analytical HPLC conditions 4:
Column: Phenomenex Hyperclone C18 BDS 5 μm×4.6 mm×150 mm
Mobile phase: A: water/acetonitrile 90/10, v/v, 0.15% TFA.
B: acetonitrile/water 90/10, v/v, 0.15% TFA
Flow rate: 1 mL/min

| Gradient: | |
|---|---|
| Time (mins) | % mobile phase A |
| 0 | 100% |
| 20 | 40% |
| 21 | 0% |
| 23 | 0% |
| 23.5 | 100 |
| 25 | 100 |
| Detection: | 210, 254 nm |
| Injection volume: | 20 μL |

General Method 3b: Coupling of Individual Enantiomers to Nonapeptide

The enantiomerically pure amino acids were coupled to the N terminal of the nonapeptide compounds using the same conditions as described above in General method 3a for the enantiomerically mixed amino acids.

Compound Examples 5 and 6

Coupling 4-((tert-butoxycarbonyl)amino)-3-(3-chlorophenyl)butanoic acid (isomer 2) (Retention time 3.46 min analytical method 1 or 3.264 min analytical method 2) under the conditions of General Method 3a followed by deprotection afforded Example 5. Example (5) was assigned the (S) stereochemistry following X-ray determination of the absolute configuration of 4-amino-3-(3-chlorophenyl)butanoic acid derived from 4-((tert-butoxycarbonyl)amino)-3-(3-chlorophenyl)butanoic acid (isomer 2).

Coupling the 4-((tert-butoxycarbonyl)amino)-3-(3-chlorophenyl)butanoic acid (isomer 1, retention time 2.89 mins analytical method 1 or 2.796 mins analytical method 2) under the conditions of General Method 3a followed by deprotection afforded Example 6. Example (6) was assigned the (R) stereochemistry following X-ray determination of the absolute configuration of 4-amino-3-(3-chlorophenyl) butanoic acid derived from 4-((tert-butoxycarbonyl)amino)-3-(3-chlorophenyl)butanoic acid (isomer 1).

General Method 4: Conversion to Acetate Salt

AG1-X2 resin (Bio-Rad Laboratories Ltd) acetate form 200-4-mesh, was regenerated by washing with 10% aqueous acetic followed by 1% aqueous acetic acid, and placed in a fritted cartridge. A solution of the compound as a TFA salt in water was applied to the column, using a loading of 30 g resin to 1 g TFA salt, and the column allowed to drip under gravity, eluting with water. Product-containing fractions were combined and lyophilised to a white solid.

Analysis of final compounds was carried by HPLC using the conditions described above (Analytical HPLC conditions).

Exemplary analytical data for the compounds of Example 5 and 6, as acetate salts is given below.

Example 5: (faster isomer) $^1$H NMR of the acetate salt (400 MHz, D$_2$O): δ (ppm) 0.70 (3 H, d, J 6.1 Hz), 0.77 (3 H, d, J 6.3 Hz), 0.78-0.90 (1H, m), 1.13 (3H, d, J 6.3 Hz), 1.17 (3H, d, J 6.4 Hz), 1.36-1.52 (2H, m), 1.75-2.06 (17 H, m, includes 1.91, s, OAc), 2.10-2.30 (4H, m), 2.72-2.91 (4H, m), 3.02-3.49 (14H, m), 4.12-4.32 (8 H, m), 4.48 (1 H, dd, J 5.6, 9.0 Hz), 4.54-4.60 (1H, m), 4.63-4.68 (1H, m), 7.25-7.41(9H, m). m/z 1145 [MH$^+$], 573 [M+2H]$^{2+}$.

Example 6: (slower isomer) $^1$H NMR of the acetate salt (400 MHz, D$_2$O): δ (ppm) 0.60-0.67 (6 H, m), 0.69-0.84 (4 H, m), 1.16 (3H, d, J 6.4 Hz), 1.33-1.50 (2 H, m), 1.76-2.04 (19 H, m, includes 1.88, s, OAc), 2.06-2.26 (4 H, m), 2.67-2.86 (4 H, m), 3.00-3.46 (14 H, m), 3.98-4.04 (1 H, m) 4.14-4.30 (7H, m), 4.45 (1 H, dd, J 5.6, 9.0 Hz), 4.54 (1 H, appears as t, J 8.3 Hz), 4.72 (1 H, dd, J 5.0, 8.9 Hz), 7.20-7.40 (9 H, m). m/z 1145 [MH$^+$], 573 [M+2H]$^{2+}$.

In all examples, the diastereomers were assigned on the basis of HPLC retention time (fast and slow eluting isomers) together with the chemical shift of the Thr residue which moves from 1.13 ppm in the fast eluting isomer, to around 0.65 ppm in the slow eluting isomer.

Example Compounds

Table 1 lists example compounds of the invention. These are compounds having the general structure shown below:

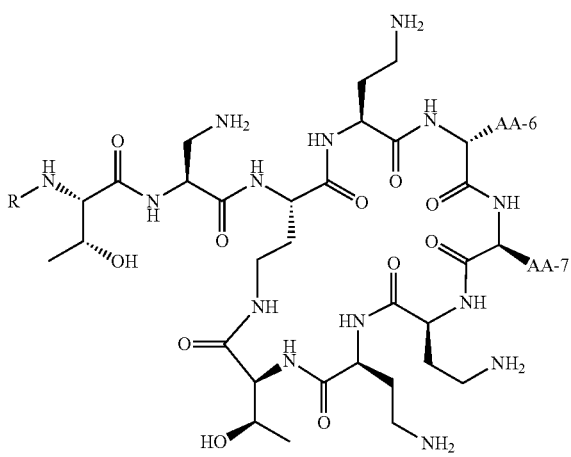

The group R corresponds to —X—R$^{15}$ in the compounds of the invention, and this group is shown in the table together with the amino acid residues at positions 6 and 7 (AA-6 and AA-7 respectively, using the polymyxin numbering system), which correspond to the groups —R$^1$ and —R$^2$ respectively, when taken together with the carbonyl group and nitrogen alpha to the carbon to which they are attached.

In these example compounds, the group —R$^3$, taken together with the carbonyl group and nitrogen alpha to the carbon to which it is attached is L-Thr, —R$^4$, together with the carbonyl group and nitrogen alpha to the carbon to which it is attached, is L-Dap (thus —R$^4$ is —CH$_2$NH$_2$), and —R$^8$, together with the carbonyl group and nitrogen alpha to the carbon to which it is attached, is L-Thr (thus —R$^8$ is methyl).

Absolute stereochemistry in the sidechain -R has been assigned by comparison to Example 5 and Example 6 which have been correlated to material of known absolute stereochemistry.

In examples 1-6 and 15-33 the determination was made by comparison of the relative retention times and the $^1$H NMR spectrum of the diastereomers (for example, taking into account the chemical shift of the Thr residue at position 2).

In Examples 7-14 the determination was made by comparison of the relative HPLC retention times of the diastereomers.

The table provides the HPLC retentions times for the example compounds. The HPLC conditions that were used for analysis are set out below.

Column: Phenomenex Hyperclone BDS C18, 4.6 mm×150 mm, 5 μm

Flow rate: 1 mL/min

Eluant:
A=10% AcN/90% Water/0.15% TFA
B=90% AcN/10% water/0.15% TFA

| Gradient: | Mins | % A | % B |
|---|---|---|---|
| | 0 | 100 | 0 |
| | 20 | 40 | 60 |
| | 21 | 0 | 100 |
| | 23 | 0 | 100 |
| | 23.5 | 100 | 0 |
| | 25 | 100 | 0 |
| Detection: 210, 254 nm | | | |

TABLE 1

Example Compounds

| Ex. | Name | —R | AA-6 | AA-7 | General Method | Formula | Mass | HPLC $t_R$ (min.) | m/z |
|---|---|---|---|---|---|---|---|---|---|
| 1 | (S)-4-amino-3-(4-chlorophenyl)butanoyl-Thr-Dap-Cyclo[Dab-Dab-DPhe-Leu-Dab-Dab-Thr] | | Phe | Leu | 3a | C52H82Cl N15O12 | 1143.6 | 9.6 | 1145 [MH+] 573 [M + 2H]$^{2+}$ |
| 2 | (R)-4-amino-3-(4-chlorophenyl)butanoyl-Thr-Dap-Cyclo[Dab-Dab-DPhe-Leu-Dab-Dab-Thr] | | Phe | Leu | 3a | C52H82Cl N15O12 | 1143.6 | 9.7 | 1145 [MH+] 573 [M + 2H]$^{2+}$ |
| 3 | (S)-4-amino-3-(2-chlorophenyl)butanoyl-Thr-Dap-Cyclo[Dab-Dab-DPhe-Leu-Dab-Dab-Thr] | | Phe | Leu | 3a | C52H82Cl N15O12 | 1143.6 | 9.1 | 1145 [MH+] 573 [M + 2H]$^{2+}$ |

TABLE 1-continued

Example Compounds

| Ex. | Name | —R | AA-6 | AA-7 | General Method | Formula | Mass | HPLC $t_R$ (min.) | m/z |
|---|---|---|---|---|---|---|---|---|---|
| 4 | (R)-4-amino-3-(2-chlorophenyl)butanoyl-Thr-Dap-Cyclo[Dab-Dab-DPhe-Leu-Dab-Dab-Thr] | (2-chlorophenyl structure) | Phe | Leu | 3a | C52H82Cl N15O12 | 1143.6 | 9.4 | 1145 [MH+] 573 [M + 2H]$^{2+}$ |
| 5 | (S)-4-amino-3-(3-chlorophenyl)butanoyl-Thr-Dap-Cyclo[Dab-Dab-DPhe-Leu-Dab-Dab-Thr] | (3-chlorophenyl structure) | Phe | Leu | 3a, 3b | C52H82Cl N15O12 | 1143.6 | 9.6 | 1145 [MH+] 573 [M + 2H]$^{2+}$ |
| 6 | (R)-4-amino-3-(3-chlorophenyl)butanoyl-Thr-Dap-Cyclo[Dab-Dab-DPhe-Leu-Dab-Dab-Thr] | (3-chlorophenyl structure) | Phe | Leu | 3a, 3b | C52H82Cl N15O12 | 1143.6 | 9.8 | 1145 [MH+] 573 [M + 2H]$^{2+}$ |
| 7 | (R)-4-amino-3-benzylbutanoyl-Thr-Dap-Cyclo[Dab-Dab-DLeu-Leu-Dab-Dab-Thr]. Isomer 1 | (benzyl structure) | Leu | Leu | 3a | C50H87 N15O12 | 1089.7 | 8.8 | 1091 [MH+] 546 [M + 2H]$^{2+}$ |
| 8 | (S)-4-amino-3-benzylbutanoyl-Thr-Dap-Cyclo[Dab-Dab-DLeu-Leu-Dab-Dab-Thr]. Isomer 2 | (benzyl structure) | Leu | Leu | 3a | C50H87 N15O12 | 1089.7 | 9.1 | 1091 [MH+] 546 [M + 2H]$^{2+}$ |
| 9 | (R)-4-amino-3-benzylbutanoyl-Thr-Dap-Cyclo[Dab-Dab-DPhe-Leu-Dab-Dab-Thr]. Isomer 1 | (benzyl structure) | Phe | Leu | 3a | C53H85 N15O12 | 1123.7 | 10.7 | 1125 [MH+] 563 [M + 2H]$^{2+}$ |
| 10 | (S)-4-amino-3-benzylbutanoyl-Thr-Dap-Cyclo[Dab-Dab-DPhe-Leu-Dab-Dab-Thr]. Isomer 2 | (benzyl structure) | Phe | Leu | 3a | C53H85 N15O12 | 1123.7 | 11.0 | 1125 [MH+] 563 [M + 2H]$^{2+}$ |
| 11 | (R)-4-amino-3-(3-chlorobenzyl)butanoyl-Thr-Dap-Cyclo[Dab-Dab-DPhe-Leu-Dab-Dab-Thr]. Isomer 1 | (3-chlorobenzyl structure) | Phe | Leu | 3a | C53H84Cl N15O12 | 1157.6 | 11.0 | 1159 [MH+] 580 [M + 2H]$^{2+}$ |

TABLE 1-continued

Example Compounds

| Ex. | Name | —R | AA-6 | AA-7 | General Method | Formula | Mass | HPLC $t_R$ (min.) | m/z |
|---|---|---|---|---|---|---|---|---|---|
| 12 | (S)-4-amino-3-(3-chlorobenzyl)butanoyl-Thr-Dap-Cyclo[Dab-Dab-DPhe-Leu-Dab-Dab-Thr]. Isomer 2 | 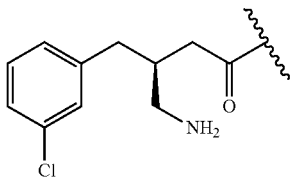 [SMILES: *C(=O)C[C@@H](CN)Cc1cccc(Cl)c1] | Phe | Leu | 3a | C53H84Cl N15O12 | 1157.6 | 11.4 | 1159 [MH+] 580 [M + 2H]$^{2+}$ |
| 13 | (S)-4-amino-3-(3-chlorobenzyl)butanoyl-Thr-Dap-Cyclo[Dab-Dab-DLeu-Leu-Dab-Dab-Thr]. Isomer 2 | 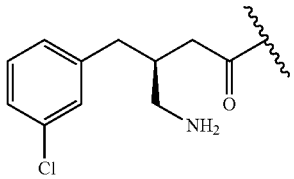 [SMILES: *C(=O)C[C@@H](CN)Cc1cccc(Cl)c1] | Leu | Leu | 3a | C50H86Cl N15O12 | 1123.6 | 10.4 | 1125 [MH+] 563 [M + 2H]$^{2+}$ |
| 14 | (R)-4-amino-3-(3-chlorobenzyl)butanoyl-Thr-Dap-Cyclo[Dab-Dab-DLeu-Leu-Dab-Dab-Thr]. Isomer 1 | 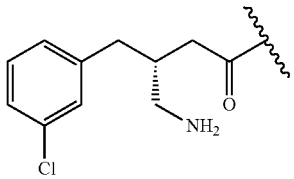 [SMILES: *C(=O)C[C@H](CN)Cc1cccc(Cl)c1] | Leu | Leu | 3a | C50H86Cl N15O12 | 1123.6 | 9.9 | 1125 [MH+] 563 [M + 2H]$^{2+}$ |
| 15 | (S)-4-amino-3-(3-isopropylphenyl) butanoyl-Thr-Dap-Cyclo[Dab-Dab-DLeu-Leu-Dab-Dab-Thr] | 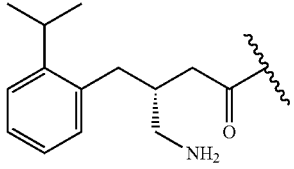 [SMILES: *C(=O)C[C@H](CN)Cc1ccccc1C(C)C] | Leu | Leu | 3a | C52H91 N15O12 | 1117.7 | 10.7 | 1119 [MH+] 560 [M + 2H]$^{2+}$ |
| 16 | (R)-4-amino-3-(3-isopropylphenyl) butanoyl-Thr-Dap-Cyclo[Dab-Dab-DLeu-Leu-Dab-Dab-Thr] | 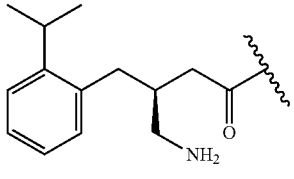 [SMILES: *C(=O)C[C@@H](CN)Cc1ccccc1C(C)C] | Leu | Leu | 3a | C52H91 N15O12 | 1117.7 | 10.9 | 1119 [MH+] 560 [M + 2H]$^{2+}$ |
| 17 | (S)-4-amino-3-(3-isopropylphenyl) butanoyl-Thr-Dap-Cyclo[Dab-Dab-DPhe-Leu-Dab-Dab-Thr] | 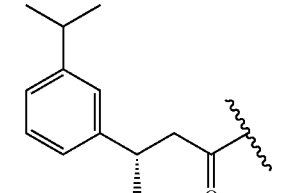 | Phe | Abu | 1 | C53H85 N15O12 | 1123.7 | 9.2 | 1125 [MH+] 563 [M + 2H]$^{2+}$ |
| 18 | (R)-4-amino-3-(3-isopropylphenyl) butanoyl-Thr-Dap-Cyclo[Dab-Dab-DPhe-Leu-Dab-Dab-Thr] | 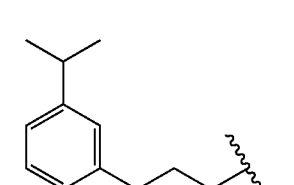 | Phe | Abu | 1 | C53H85 N15O12 | 1123.7 | 9.4 | 1125 [MH+] 563 [M + 2H]$^{2+}$ |

TABLE 1-continued

Example Compounds

| Ex. | Name | —R | AA-6 | AA-7 | General Method | Formula | Mass | HPLC $t_R$ (min.) | m/z |
|---|---|---|---|---|---|---|---|---|---|
| 19 | (S)-4-amino-3-(3-isopropylphenyl)butanoyl-Thr-Dap-Cyclo[Dab-Dab-DLeu-Thr-Dab-Dab-Thr] | 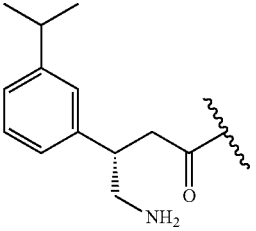 [SMILES: *C(=O)C[C@H](CN)c1cccc(C(C)C)c1] | Leu | Thr | 1 | C50H87 N15O13 | 1105.7 | 7.6 | 1107 [MH+] 554 [M + 2H]$^{2+}$ |
| 20 | (R)-4-amino-3-(3-isopropylphenyl)butanoyl-Thr-Dap-Cyclo[Dab-Dab-DLeu-Thr-Dab-Dab-Thr] | 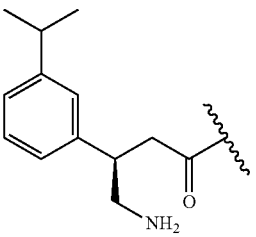 [SMILES: *C(=O)C[C@@H](CN)c1cccc(C(C)C)c1] | Leu | Thr | 1 | C50H87 N15O13 | 1105.7 | 7.8 | 1107 [MH+] 554 [M + 2H]$^{2+}$ |
| 21 | (S)-4-amino-3-(m-tolyl)butanoyl-Thr-Dap-Cyclo[Dab-Dab-DPhe-Leu-Dab-Dab-Thr] | 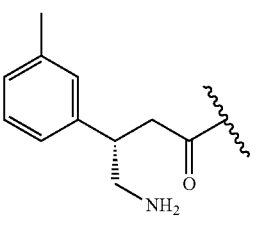 [SMILES: *C(=O)C[C@H](CN)c1cccc(C)c1] | Phe | Leu | 3a | C53H85 N15O12 | 1123.7 | 8.7 | 1125 [MH+] 563 [M + 2H]$^{2+}$ |
| 22 | (R)-4-amino-3-(m-tolyl)butanoyl-Thr-Dap-Cyclo[Dab-Dab-DPhe-Leu-Dab-Dab-Thr] | 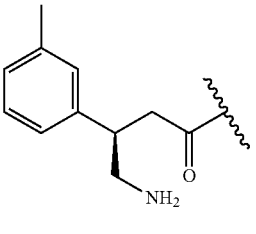 [SMILES: *C(=O)C[C@@H](CN)c1cccc(C)c1] | Phe | Leu | 3a | C53H85 N15O12 | 1123.7 | 8.9 | 1125 [MH+] 563 [M + 2H]$^{2+}$ |
| 23 | (S)-4-amino-3-(3-chlorophenyl)butanoyl-Thr-Dap-Cyclo[Dab-Dab-DLeu-Abu-Dab-Dab-Thr] | 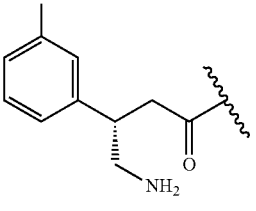 | Leu | Abu | 2 | C47H80Cl N15O12 | 1081.6 | 9.2 | 1083 [MH+] 542 [M + 2H]$^{2+}$ |
| 24 | (S)-3-([1,1'-biphenyl]-3-yl)-4-aminobutanoyl-Thr-Dap-Cyclo[Dab-Dab-DLeu-Abu-Dab-Dab-Thr] | 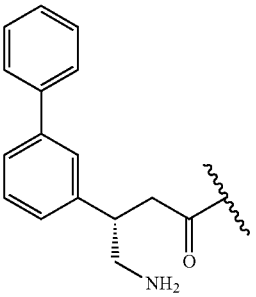 [SMILES: *C(=O)C[C@H](CN)c1cccc(-c2ccccc2)c1] | Leu | Abu | 3b | C53H85 N15O12 | 1123.7 | 8.5 | 1125 [MH+] 563 [M + 2H]$^{2+}$ |

TABLE 1-continued

Example Compounds

| Ex. | Name | —R | AA-6 | AA-7 | General Method | Formula | Mass | HPLC $t_R$ (min.) | m/z |
|---|---|---|---|---|---|---|---|---|---|
| 25 | (R)-3-([1,1'-biphenyl]-3-yl)-4-aminobutanoyl-Thr-Dap-Cyclo[Dab-Dab-DLeu-Abu-Dab-Dab-Thr] | biphenyl-CH(CH2NH2)-CH2-C(=O)- | Leu | Abu | 3b | C53H85N15O12 | 1123.7 | 8.7 | 1125 [MH+] 563 [M + 2H]$^{2+}$ |
| 26 | (S)-4-amino-3-(3-isobutylphenyl)butanoyl-Thr-Dap-Cyclo[Dab-Dab-DLeu-Abu-Dab-Dab-Thr] | 3-isobutylphenyl-CH(CH2NH2)-CH2-C(=O)- | Leu | Abu | 3a | C51H89N15O12 | 1103.7 | 8.9 | 1105 [MH+] 553 [M + 2H]$^{2+}$ |
| 27 | (R)-4-amino-3-(3-isobutylphenyl)butanoyl-Thr-Dap-Cyclo[Dab-Dab-DLeu-Abu-Dab-Dab-Thr] | 3-isobutylphenyl-CH(CH2NH2)-CH2-C(=O)- | Leu | Abu | 3a | C51H89N15O12 | 1103.7 | 9.1 | 1105 [MH+] 553 [M + 2H]$^{2+}$ |
| 28 | (S)-4-amino-3-(3,5-dichlorophenyl)butanoyl--Thr-Dap-Cyclo[Dab-Dab-DnorLeu-Abu-Dab-Dab-Thr] | 3,5-dichlorophenyl-CH(CH2NH2)-CH2-C(=O)- | Norleu | Abu | 2 | C47H79Cl2N15O12 | 1115.5 | 8.0 | 1117 [MH+] 559 [M + 2H]$^{2+}$ |
| 29 | (R)-4-amino-3-(3,5-dichlorophenyl)butanoyl--Thr-Dap-Cyclo[Dab-Dab-DnorLeu-Abu-Dab-Dab-Thr] | 3,5-dichlorophenyl-CH(CH2NH2)-CH2-C(=O)- | Norleu | Abu | 2 | C47H79Cl2N15O12 | 1115.5 | 8.1 | 1117 [MH+] 559 [M + 2H]$^{2+}$ |

TABLE 1-continued

Example Compounds

| Ex. | Name | —R | AA-6 | AA-7 | General Method | Formula | Mass | HPLC $t_R$ (min.) | m/z |
|---|---|---|---|---|---|---|---|---|---|
| 30 | (S)-4-amino-3-(3-(thiophen-3-yl)phenyl)butanoyl-Thr-Dap-Cyclo[Dab-Dab-DLeu-Abu-Dab-Dab-Thr] | 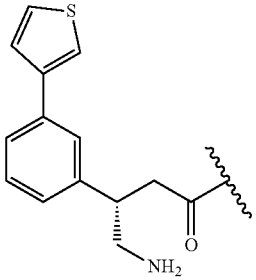 [SMILES: *C(=O)C[C@H](CN)c1cccc(-c2ccsc2)c1] | Leu | Abu | 3a | C51H83N15O12S | 1129.6 | 8.4 | 1131 [MH+] 566 [M + 2H]$^{2+}$ |
| 31 | (R)-4-amino-3-(3-(thiophen-3-yl)phenyl)butanoyl-Thr-Dap-Cyclo[Dab-Dab-DLeu-Abu-Dab-Dab-Thr] | 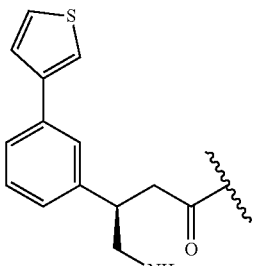 | Leu | Abu | 3a | C51H83N15O12S | 1129.6 | 8.5 | 566 [M + 2H]$^{2+}$ |
| 32 | (S)-4-amino-3-(3-bromophenyl)butanoyl-Thr-Dap-Cyclo[Dab-Dab-DLeu-Abu-Dab-Dab-Thr] | 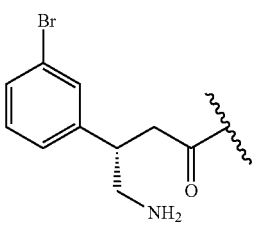 [SMILES: *C(=O)C[C@H](CN)c1cccc(Br)c1] | Leu | Abu | 3a | C47H80BrN15O12 | 1125.5 | 7.1 | 1128 [MH+] 564 [M + 2H]$^{2+}$ |
| 33 | (R)-4-amino-3-(3-bromophenyl)butanoyl-Thr-Dap-Cyclo[Dab-Dab-DLeu-Abu-Dab-Dab-Thr]. | 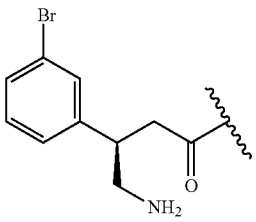 | Leu | Abu | 3a | C47H80BrN15O12 | 1125.5 | 7.5 | 1128 [MH+] 564 [M + 2H]$^{2+}$ |

Biological Results

The compounds of the invention were tested, and the results were compared to comparative examples, which includes compounds previously reported in the art.

MIC Determination

The inoculum was prepared by making a direct suspension of isolated colonies (selected from an 18-24 hour Mueller-Hinton agar plate) adjusted to the 0.5 McFarland standard. MIC testing was performed by two-fold serial antibiotic dilutions in cation-adjusted Mueller-Hinton Broth in sterile 96-well microtitre plates in a total volume of 170 µL (150 µL broth containing the antimicrobial agent, 20 µL inoculum). The assays were performed in duplicate. Plates were incubated aerobically without shaking for 18-20 hours at 35° C. with the MIC defined as the lowest concentration of drug that prevented visible growth. Several of the compounds were subjected to multiple tests, and where this is the case, the MIC presented is the median value obtained. The MIC values are quoted in µg/mL.

In Vitro Renal Cell Toxicity Assay

The in vitro renal cell toxicity assay was performed according to the following protocol.

HK-2 cells were maintained and assayed in Keratinocyte-SFM media supplemented with 5 ng/mL Epidermal Growth Factor (EGF) and 50 µg/mL Bovine Pituitary Extract (BPE). Cells were seeded at 7,500 cells per well in 96-well plates and allowed to adhere overnight. Polymyxin B (PMB) and test compounds were dissolved in 10% DMSO in water to give a stock solution of 20 and 60 mg/mL, respectively. The test compounds were diluted to give a top concentration of 3,000 or 1,000 µg/mL with semi-log dilutions to give a 9-point concentration range plus vehicle control. PMB was also diluted to give a top concentration of 1,000 µg/ml with semi-log dilutions. Water and DMSO levels were kept constant at 5% and 0.5% respectively. The test compounds were incubated with cells for 24 h at 37° C. 5% CO$_2$ in a humidified atmosphere. CellTiter-Blue was diluted in PBS (1:4) and added 20% (v/v) and incubated at 37° C. for 2 h before fluorescent product was detected.

Media only background values were subtracted before the data was analysed using GraphPad Prism. Individual values were normalised to the vehicle control wells for each compound. Compound concentration values were plotted as log values to enable a dose-response curve to be fitted. The bottom of the curve was constrained to zero and $IC_{50}$ values were determined.

concentration of 0.167 grams of kidney/gram of homogenate.

Kidney homogenates (100 μL) were mixed with methanol (190 μL) and TFA (110 μL, 10% v/v in water) and stored overnight at −20° C. for protein precipitation. After 10 min. centrifugation at 13,000 rpm and 6° C., 200 μl of the supernatants were transferred into glass inserts and analysed by LC-MS-MS.

TABLE 2

Biological Results

| Ex. | AlogP | E. coli ATCC CA58 25922 | | K. pneumoniae CA64 ATCC 13822 | | P. aeruginosa CCUG 59347 ATCC 27853 | | A. baumannii NCTC 13424 ATCC BAA-747 | | HK-2 rel to PMB | 4 hr kidney level (μg/g)* | 4 hr kidney level/Rel HK-2 |
|---|---|---|---|---|---|---|---|---|---|---|---|---|
| 1 | −6.3 | 4 | 0.125 | 8 | 0.125 | 0.25 | 0.06 | 0.06 | 0.06 | 8.8 | 267 | 30 |
| 2 | −6.3 | 8 | 0.25 | 2 | 0.25 | 0.5 | 0.25 | 0.25 | 0.25 | 7.2 | 538 | 75 |
| 3 | −6.3 | 32 | 1 | 65 | 0.5 | 0.5 | 0.5 | 1 | 2 | ND | ND | ND |
| 4 | −6.3 | 16 | 0.5 | 16 | 0.25 | 0.5 | 0.25 | 1 | 1 | ND | ND | ND |
| 5 | −6.3 | 8 | 0.125 | 16 | 0.125 | 0.25 | 0.25 | 0.06 | 0.125 | 11.6 | 170 | 15 |
| 6 | −6.3 | 8 | 0.125 | 8 | 0.125 | 0.5 | 0.125 | 0.5 | 0.5 | 7.8 | 381 | 49 |
| 7 | −6.9 | 16 | 0.25 | 32 | ND | 0.25 | 0.125 | 0.125 | 0.125 | ND | ND | ND |
| 8 | −6.9 | 16 | 0.125 | 32 | ND | 0.5 | 0.06 | 0.25 | 0.125 | ND | ND | ND |
| 9 | −6.5 | 8 | 0.25 | 64 | 0.25 | 0.5 | 0.125 | 0.125 | 0.25 | 12.0 | 159 | 13 |
| 10 | −6.5 | 8 | 0.125 | 16 | 0.5 | 0.25 | 0.125 | 0.25 | 0.25 | 8 | 346 | 43 |
| 11 | −5.9 | 4 | 0.5 | 16 | 0.5 | 0.5 | 0.25 | 0.25 | 0.5 | 5.2 | 163 | 32 |
| 12 | −5.9 | 4 | 0.5 | 8 | 0.5 | 0.5 | 0.125 | 0.25 | 0.25 | ND | ND | ND |
| 13 | −6.2 | 8 | 0.5 | 16 | 0.5 | 0.5 | 0.25 | 0.5 | 0.5 | ND | ND | ND |
| 14 | −6.2 | 8 | 1 | 32 | 0.5 | 1 | 0.5 | 0.5 | 0.5 | ND | ND | ND |
| 15 | −6.1 | 4 | 0.125 | 16 | 0.125 | 0.5 | 0.25 | 0.06 | 0.06 | 52.1 | 443 | 8.5 |
| 16 | −6.1 | 16 | 0.5 | 8 | 0.25 | 1 | 0.5 | 0.5 | 0.5 | ND | ND | ND |
| 17 | −6.5 | 8 | 0.125 | 16 | 0.125 | 0.25 | 0.125 | 0.06 | 0.06 | 29.0 | 231 | 8 |
| 18 | −6.5 | 16 | 0.25 | 8 | 0.25 | 0.25 | 0.25 | 0.125 | 0.125 | 32.8 | 535 | 16.3 |
| 19 | −7.9 | 32 | 0.25 | 64 | 0.25 | 1 | 0.25 | 0.25 | 0.25 | 101.4 | 386 | 4 |
| 20 | −7.9 | 64 | 1 | 64 | 2 | 2 | 0.5 | 1 | 2 | ND | ND | ND |
| 21 | −6.5 | 16 | 0.125 | 32 | 0.25 | 0.5 | 0.25 | 0.125 | 0.125 | 26.7 | 209 | 8 |
| 23 | −7.4 | 32 | 0.125 | 64 | 0.125 | 0.5 | 0.25 | 0.125 | ND | >41 | 263 | <6.4 |
| 22 | −6.5 | 16 | 0.25 | 8 | 0.25 | 0.5 | 0.25 | 1 | 1 | ND | ND | ND |
| 24 | −6.5 | 4 | 0.125 | 16 | 0.25 | 0.25 | 0.125 | 0.06 | 0.03 | 21.8 | 203 | 9 |
| 25 | −6.5 | 16 | 0.25 | 2 | 0.5 | 0.5 | 0.25 | 0.125 | 0.125 | ND | ND | ND |
| 26 | −6.4 | 8 | 0.06 | 8 | 0.5 | 0.5 | 0.25 | 0.03 | 0.06 | >58 | 353 | <6.1 |
| 27 | −6.4 | 16 | 0.25 | 2 | 0.25 | 0.5 | 0.5 | 0.125 | 0.125 | ND | ND | ND |
| 28 | −6.5 | 16 | 0.125 | 8 | 0.125 | 0.25 | 0.25 | 0.06 | 0.125 | 68.5 | 408 | 6.0 |
| 29 | −6.5 | 16 | 0.25 | 8 | 0.25 | 0.5 | 0.25 | 0.125 | 0.125 | ND | ND | ND |
| 30 | −6.8 | 8 | 0.125 | 16 | 0.125 | 0.5 | 0.25 | 0.06 | ND | 37.5 | 252 | 6.7 |
| 31 | −6.8 | 16 | 0.125 | 4 | 0.25 | 0.25 | 0.25 | 0.125 | ND | ND | ND | ND |
| 32 | −7.3 | 32 | 0.25 | 32 | 0.5 | 0.5 | 0.5 | 0.125 | 0.125 | ND | ND | ND |
| 33 | −7.3 | 64 | 0.5 | 16 | 0.5 | 0.5 | 0.5 | 1 | 1 | ND | ND | ND |

ND—not determined (not tested)

$IC_{50}$ values are expressed relative to that for PMB in the same experiment. Where multiple determinations have been made, median values are presented.

Four Hour Kidney Level Measurements

Compounds were dosed subcutaneously at 17.2 mg/kg free base to mice (n=2 or 3). Four hours after dosing the animals were euthanised and kidneys removed, trimmed of fat and connective tissue, weighed and immediately snap-frozen. After thawing at room temperature, pairs of kidneys from each animal were placed in 2 mL conical tubes containing pre-weighed ceria-stabilised zirconium oxide beads. Trifluoroacetic acid, TFA (0.25 mL, 0.15% v/v in water) was added and the tubes were loaded onto a FastPrep-24 homogeniser (MP Biomedicals Europe), and subjected to 3 cycles of 30 seconds each at a speed of 6 m/sec. An aliquot (200 μL) of the homogenate was diluted with a calculated volume of TFA solution (0.15% v/v in water) to give a final Additional Biological Data Comparison of Renal Toxicity—Example 5 and Reference Examples D77 and 38

Mice (n=6) were dosed subcutaneously three times per day with Polymyxin B, colistin sulphate, Reference Example D77, Reference Example 38 or Example 5 at 17.2 mg free base/kg. Starting immediately after the first dose on day 4, mice were transferred to individual metabolic cages and urine was collected over the following 24 hours for determination of biomarker levels (albumin, cystatin C, KIM-1). The geometric mean biomarker levels are presented in the table below:

| Compound | Albumin (μg/24 h) | Cystatin C (ng/24 h) | KIM-1 (ng/24 h) |
|---|---|---|---|
| PMB | 1,154-1,912 | 1,155-1,400 | 4-22 |
| Colistin | 2,353-2,548 | 1,266-1,678 | 42-89 |
| Ref. Example D77 | 3,639 | 7,542 | 130 |

| Compound | Albumin (μg/24 h) | Cystatin C (ng/24 h) | KIM-1 (ng/24 h) |
| --- | --- | --- | --- |
| Ref. Example 38 | 2,362 | 14,015 | 79 |
| Example 5 | 1,004 | 827 | 3 |

PMB values show the range from 4 experiments and colistin from 2 experiments.

Elevation of albumin, cystatin C or KIM-1 in the urine are signs of renal damage. Example 5 showed the lowest levels of all 3 biomarkers of renal toxicity.

Reference Example D77 is described in WO 2015/135976. Reference Example 38 is described in WO 2016/083531.

Comparison of Renal Toxicity—Examples 5, 9 and 17

Mice (n=6) were dosed subcutaneously with PMB, Example 5, Example 9 or Example 17 at 25 mg free base/kg for four doses at 8 hr intervals. After the fourth dose animals were transferred into individual metabolic cages and urine collected for 24 hours for determination of urinary biomarkers. After collecting urine mice were euthanised and the kidneys harvested for histopathology.

| Compound | Albumin (μg/24 h) | Cystatin C (ng/24 h) | KIM-1 (ng/24 h) |
| --- | --- | --- | --- |
| PMB | 1,147 | 1,425 | 58 |
| Example 5 | 343 | 448 | 1 |
| Example 9 | 749 | 754 | 2 |

None of the animals in the Example 5 or Example 9 groups showed any signs of degeneration or regeneration by histopathology. In contrast all 6 animals treated with PMB showed minimal tubular regeneration.

In a separate experiment Example 17 was compared with PMB.

| Compound | Elevation Compared With Vehicle Control | | |
| --- | --- | --- | --- |
| | Albumin | Cystatin C | KIM-1 |
| PMB | 29× | 2× | 771× |
| Example 17 | 2.7× | 1.8× | 4.7× |

Histopathology signs were also assessed:

| | PMB | Example 17 |
| --- | --- | --- |
| Tubular degeneration/necrosis | 4 normal/1 minimal | All normal |
| Basophilic tubules | 4 minimal/1 mild | 3 normal/2 minimal |

Comparison of Renal toxicity of Example 5 and PMB in Cynomolgus Monkey

Male Cynomolgus monkeys (n=3) were dosed by intravenous infusion over 1 h at 20 mg/kg/dose, 3 times per day for 7 days with Example 5. In a separate experiment male monkeys (n=3) were dosed with PMB for the same period at 4 mg/kg/dose. In both experiments control animals were dosed 3 times per day with saline.

At the end of the 7 day period blood was sampled and the serum levels of blood urea nitrogen and creatinine determined as indicators of renal damage. In the case of Example 5 the mean BUN and creatinine levels were elevated less than 50% compared to the saline control animals. However for animals dosed with PMB the BUN level was elevated 76% compared to control animals and the creatinine level was 2.6× higher.

Kidneys were harvested at the end of the 7 day dosing period and examined microscopically. Of the three animals treated with PMB, 2 showed mild tubular degeneration and 1 minimal. Of the animals treated with Example 5, 1 showed mild tubular degeneration and 2 showed minimal degeneration.

The dose in these experiments was 5× higher for Example 5 than PMB but signs of renal toxicity were reduced. The drug exposure from one dosing cycle on day 7 of dosing (AUC0-8 hr) was 234 μg·hr/mL for Example 5 and 117 μg·hr/mL for PMB.

Efficacy of Compounds in a Neutropenic Murine Thigh Model Infected with *E. coli* ATCC 25922

After rendering neutropenic (cyclophosphamide 150 mg/kg d-4, 100 mg/kg d-1), CD-1 mice (n=5) were inoculated in each thigh with approx. 105 cfu of *E. coli* ATCC25922. Mice were dosed IV with 0.125, 0.5, and 3 mg/kg of PMB sulphate or test compound (equivalent weight free base) at 1, 3.5 and 6 h post-infection. At 9 h post-infection mice were euthanised and thighs prepared for colony counts.

The decrease in colony counts relative to a vehicle control is shown in the table below. In each case the decrease observed with PMB in the same experiment is shown in parentheses:

| Compound | Log drop in cfu Compared to Vehicle Control | | |
| --- | --- | --- | --- |
| | 0.125 mg/kg | 0.5 mg/kg | 3 mg/kg |
| Example 5 | 0.1 (0.4) | 2.2 (2.6) | 3.4 (3.5) |
| Example 9 | 0.1 (0.4) | 0.5 (0.6) | 3.7 (3.9) |
| Example 17 | 0 (0.1) | 1.3 (1.1) | 3.7 (3.7) |
| Example 24 | 0 (0) | 0.4 (0.5) | 2.4 (2.9) |

All compounds were similarly efficacious to PMB.

Efficacy of Compounds in a Neutropenic Murine Thigh Model Infected with *K. Pneumoniae* ATCC 43816

After rendering neutropenic (cyclophosphamide 150 mg/kg d-4, 100 mg/kg d-1), CD-1 mice (n=5) were inoculated in each thigh with approx. 105 cfu of *K. pneumoniae* ATCC43816. Mice were dosed IV with appropriate doses of PMB sulphate or test compound (equivalent weight free base) at 2, 6 and 10 h post-infection. At 16 h post-infection mice were euthanised and thighs prepared for colony counts.

The decrease in colony counts relative to a vehicle control is shown in the table below. In each case the decrease observed with PMB in the same experiment is shown in parentheses:

| Dose (mg/kg) | Log drop in cfu Compared to Vehicle Control | |
| --- | --- | --- |
| | Example 5 | Example 24 |
| 0.125 | 0 (0.2) | 0 (0.2) |
| 0.25 | ND | 0.2 (0.2) |
| 0.5 | 4.8 (4.9) | 0.2 (0.9) |

| Dose | Log drop in cfu Compared to Vehicle Control | |
|---|---|---|
| (mg/kg) | Example 5 | Example 24 |
| 1 | 4.8 (5.2) | ND |
| 2 | ND | 4.7 (4.0) |
| 4 | 5.3 (5.6) | ND |

ND = Not determined

Both compounds were similarly efficacious to PMB.

Efficacy of Compounds in a Neutropenic Murine Thigh Model Infected with *A. baumannii* NCTC13301

After rendering neutropenic (cyclophosphamide 150 mg/kg d-4, 100 mg/kg d-1), CD-1 mice (n=5) were inoculated in each thigh with approx. 105 cfu of *A. baumannii* NCTC13301. Mice were dosed IV with 0.125, 0.5, 1 and 4 mg/kg of PMB sulphate or test compound (equivalent weight free base) at 2, 6 and 10 h post-infection. At 16 h post-infection mice were euthanised and thighs prepared for colony counts.

The decrease in colony counts relative to a vehicle control is shown in the table below. In each case the decrease observed with PMB in the same experiment is shown in parentheses:

| Dose | Log Drop in cfu Compared to Vehicle Control | |
|---|---|---|
| (mg/kg) | Example 5 | Example 24 |
| 0.125 | 0.4 (0.3) | 0.1 (0.1) |
| 0.5 | 3.1 (4.2) | 2.2 (4.1) |
| 1 | 6.7 (5.8) | 5.5 (5.0) |
| 4 | 7.4 (6.5) | 5.7 (5.3) |

Both compounds were similarly efficacious to PMB.

Efficacy of Compounds in a Neutropenic Murine Lung Model Infected with *A. baumannii* NCTC13301

After rendering neutropenic (cyclophosphamide 200 mg/kg d-4, 150 mg/kg d-1), CD-1 mice (n=8) were inoculated intranasally with approx. 107 cfu per lung of *A. baumannii* NCTC13301. Mice were dosed SC with PMB sulphate (20 mg/kg) or appropriate doses of test compound (equivalent weight free base) at 2, 6 and 10 h post-infection. At 16 h post-infection mice were euthanised and lungs prepared for colony counts.

The decrease in colony counts relative to a vehicle control is shown in the table below. In each case the decrease observed with PMB in the same experiment is shown in parentheses:

| Dose | Log Drop in cfu Compared to Vehicle Control | |
|---|---|---|
| (mg/kg) | Example 5 | Example 24 |
| 2.5 | 0 | 0.9 |
| 10 | 0 | 1.6 |
| 20 | 2.5 (0) | 2.7 (0) |
| 30 | 4.0 | 3.9 |

PMB was not efficacious in this model at the maximum tolerated dose. Example 5 was more effective at 20 mg/kg and could also be dosed at higher levels to achieve a greater effect due to reduced toxicity.

Efficacy of Compounds in a Neutropenic Murine Lung Model Infected with *P. aeruginosa* ATCC 27853

After rendering neutropenic (cyclophosphamide 200 mg/kg d-4, 150 mg/kg d-1), CD-1 mice (n=8) were inoculated intranasally with 104-105 cfu per lung of *P. aeruginosa* ATCC27853. Mice were dosed SC with appropriate doses of PMB sulphate or test compound (equivalent weight free base) at 2, 6 and 10 h post-infection. At 16 h post-infection mice were euthanised and lungs prepared for colony counts.

The decrease in colony counts relative to a vehicle control is shown in the table below. In each case the decrease observed with PMB in the same experiment is shown in parentheses:

| Dose | Log drop in cfu compared to vehicle control | |
|---|---|---|
| (mg/kg) | Example 5 | Example 24 |
| 2.5 | 0 (0) | 0.8 (0.3) |
| 5 | 0 (0) | ND |
| 7.5 | ND | 3.2 (1.0) |
| 10 | 2 (0.7) | ND |
| 20 | 3.6 (2.6) | 4.4 (3.7) |
| 40 | ND | 5.7 |

ND = Not determined

Both compounds showed superior efficacy to PMB in this model.

MIC values for Example 5 in the presence of Rifampicin

| Organism | Strain Collection No. | Known Resistance Genotype | Polymyxin B (PMB) | PMB + Rif (1 µg/mL) | Example 5 | Ex. 5 + Rif (1 µg/mL) |
|---|---|---|---|---|---|---|
| *E. coli* | ATCC 25922 | NA | 0.25 | ≤0.015 | 0.125 | ≤0.015 |
| | CDF-1 | MCR-1 | 4 | 0.06 | 8 | 0.06 |
| | IHMA 940398 | NA | 16 | 0.06 | 32 | 0.125 |
| *K. pneumoniae* | ATCC 13882 | NA | 0.25 | 0.06 | 0.125 | 0.06 |
| | IHMA 580884 | NA | 8 | 0.06 | 16 | 0.125 |
| | IHMA 520329 | SHV-12, KPC-2 | 0.125 | >64 | 0.06 | |
| | | | 64 | | | |
| *P. aeruginosa* | ATCC 27853 | NA | 0.5 | 0.125 | 0.25 | 0.125 |
| | IHMA 517175 | NA | 8 | 0.25 | 8 | 0.5 |
| | IHMA 644636 | NA | 32 | 0.5 | 32 | 1 |

-continued

| Organism | Strain Collection No. | Known Resistance Genotype | Polymyxin B (PMB) | PMB + Rif (1 µg/mL) | Example 5 | Ex. 5 + Rif (1 µg/mL) |
|---|---|---|---|---|---|---|
| *A. baumannii* | NCTC 13301 | OXA-23 | 0.25 | 0.015 | 0.06 | 0.015 |
|  | IHMA 851735 | OXA-23 | 8 | 0.03 | 0.25 | 0.015 |
|  | IHMA 517303 | NA | >64 | 0.125 | >64 | 0.03 |

MIC values (µg/mL) were determined by broth microdilution under CLSI conditions.

Both PMB and Example 5 show strong synergy with rifampicin even against strains with reduced susceptibility to polymyxins.

Stereochemical Study

The compounds of the invention contain a stereocentre at the β-position of the γ-aminopropyl group in the N-terminal moiety. Surprisingly it has been found that one of the stereoisomers at this position is usually associated with lower cytotoxicity and lower kidney drug levels. This is the stereoisomer that elutes more rapidly on reverse phase chromatography.

For example, in the pair of diastereoisomers relating to Examples 5 and 6, the diastereomer which elutes faster from a reverse-phase HPLC column shows lower kidney exposure and lower cytotoxicity than the corresponding slower isomer. The faster diastereomer (Example 5) is derived from (S)-4-amino-3-(3-chlorophenyl) butanoic acid, by small-molecule X-Ray analysis of the corresponding amino acid (as shown in the scheme below).

Scheme 1

Slow Isomer on RP—HPLC
cf. Example 6

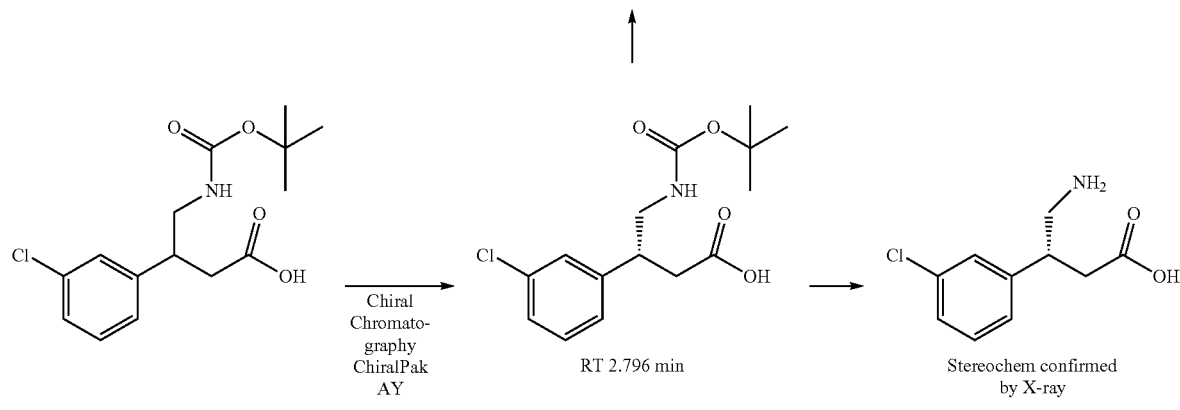

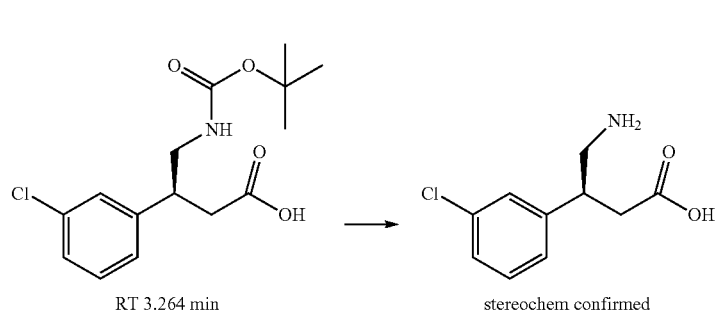

Fast Isomer on RP—HPLC
cf. Example 5

Further comparisons are shown in Table 3 below. Diastereomers (epimers in the N-terminal group) which elute more rapidly on reverse phase chromatography, and which have NMR chemical shifts similar to those given for Example 5, are likely to have the same absolute stereochemistry as Example 5, as described above.

The absolute stereochemistry assigned to each of the compounds in Table 3 is shown in Table 1.

TABLE 3

Stereochemistry Results

| Example | Structure | Cytotoxicity | Drug level in kidney | 4 hr kidney level/rel. cytotoxicity |
|---|---|---|---|---|
| 1 | Cl-C6H4-CH(CH2NH2)-CH2-C(=O)-PMBN(Dap3) 'Fast' isomer | 8.8 | 268 | 30 |
| 2 | Cl-C6H4-CH(CH2NH2)-CH2-C(=O)-PMBN(Dap3) 'Slow' isomer | 7.2 | 538 | 75 |
| 5 | 3-Cl-C6H4-CH(CH2NH2)-CH2-C(=O)-PMB-Dap3 'Fast' isomer | 11.6 | 170 | 15 |
| 6 | 3-Cl-C6H4-CH(CH2NH2)-CH2-C(=O)-PMBN-Dap3 'Slow' isomer | 7.8 | 381 | 49 |
| 9 | C6H5-CH2-CH(CH2NH2)-CH2-C(=O)-PMBN(Dap)3 Fast isomer | 12.0 | 159 | 13 |
| 10 | C6H5-CH2-CH(CH2NH2)-CH2-C(=O)-PMBN(Dap)3 Slow isomer | 8.0 | 346 | 43 |

The cytotoxicity refers to measured $IC_{50}$ relative to that recorded for Polymyxin B against a HK-2 cell line.

The drug level refers to the amount of compound found in the kidney at 4 hours after 17.2 mg/kg sc dose (μg/g) in a mouse model.

Additional Data

Renal Toxicity of Example 24 Compared with PMB after Four Doses in Mouse

Groups of male CD-1 mice (n=5) were dosed subcutaneously four times at 8 h. intervals with either Polymyxin B (PMB) at 12.5 or 25 mg free base/kg, or the compound of Example 24 at 25, 50 or 75 mg free base/kg. Immediately after the fourth dose mice were transferred to metabolic cages and urine collected for 24 h. for determination of urinary biomarkers. After urine collection mice were sacrificed for renal histopathology. Mean biomarker levels are shown in Table 4 below.

TABLE 4

Urine Biomarkers

| Compound | Dose (mg/kg) | Cystatin C | β-2 microglobulin | Kim-1 | NGAL | Albumin |
|---|---|---|---|---|---|---|
| Vehicle | — | 22.24 | 0.05 | 17.01 | 0.00 | 3.44 |
| PMB | 12.5 | 29.45 | 3.43 | 21.89 | 0.30 | 3.75 |
| PMB | 25 | 44.51 | 43.83 | 3,446.42 | 4.37 | 7.73 |
| Ex 24 | 25 | 31.04 | 0.05 | 27.61 | 0.00 | 4.78 |
| Ex 24 | 50 | 33.97 | 13.22 | 171.59 | 0.63 | 6.95 |
| Ex 24 | 75 | 81.44 | 68.51 | 1,203.41 | 3.71 | 10.93 |

The urine biomarkers were normalized to urinary creatinine.

For all five biomarkers expression at 50 mg/kg Ex 24 was lower than at 25 mg/kg PMB and for two (Kim-1, NGAL) of the five biomarkers expression at 75 mg/kg dose was lower than for PMB at 25 mg/kg.

The histopathology results is shown in Table 5 below.

TABLE 5

Histopathology Results

| Compound | Dose (mg/kg) | Tubular Degeneration/necrosis | Basophilic Tubules (cortex) | Mitotic Figures increased |
|---|---|---|---|---|
| Vehicle | — | 0/5 | 0/5 | 0/5 |
| PMB | 12.5 | 0/5 | 0/5 | 0/5 |
| PMB | 25 | 5/5 (2 min/2 moderate) | 5/5 (1 min/2 mild/2 moderate) | 3/5 (2 min/1 mild) |
| Ex. 24 | 25 | 0/5 | 0/5 | 0/5 |
| Ex. 24 | 50 | 2/5 (2 min) | 2/5 (2 min) | 2/5 (2 min) |
| Ex. 24 | 75 | 5/5 (1 min/3 mild/1 moderate)) | 5/5 (2 min/1 mild/1 moderate/1 marked) | 5/5 (5 min) |

*One animal died on study

The renal histopathology at the 50 mg/kg dose of Example 24 was less severe than for PMB at a dose of 25 mg/kg, and the renal histopathology was similar at a 75 mg/kg dose of Example 24 compared with a dose of PMB at 25 mg/kg.

REFERENCES

All documents mentioned in this specification are incorporated herein by reference in their entirety.

de Visser et al. *J. Peptide Res*, 61, 2003, 298
Dolomanov et al. *J. AppL Cryst.* 42, 2009, 339
Felluga et al. *Tetrahedron Asymmetry*, 19, 2008, 945
Sheldrick *Acta Cryst.* A71, 2015, 3-8
Sheldrick *Acta Cryst.* C71, 2015, 3-8
Vaara et al. *Antimicrob. Agents and Chemotherapy*, 52, 2008. 3229
Velkov et al. *ACS Chem. Biol.* 9, 2014, 1172
Velkov et al. *ACS Chem. Biol.* 9, 2014, 1172
WO 2014/188178
WO 2016/083531
WO 2013/072695
WO 2015/135976

The invention claimed is:

1. A compound of the formula:

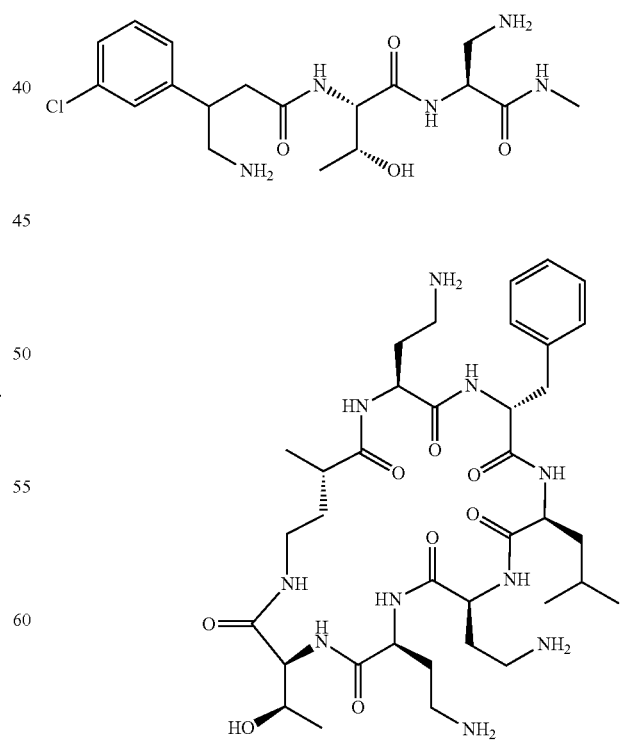

and salts, solvates and protected forms thereof.

2. A compound of the formula:

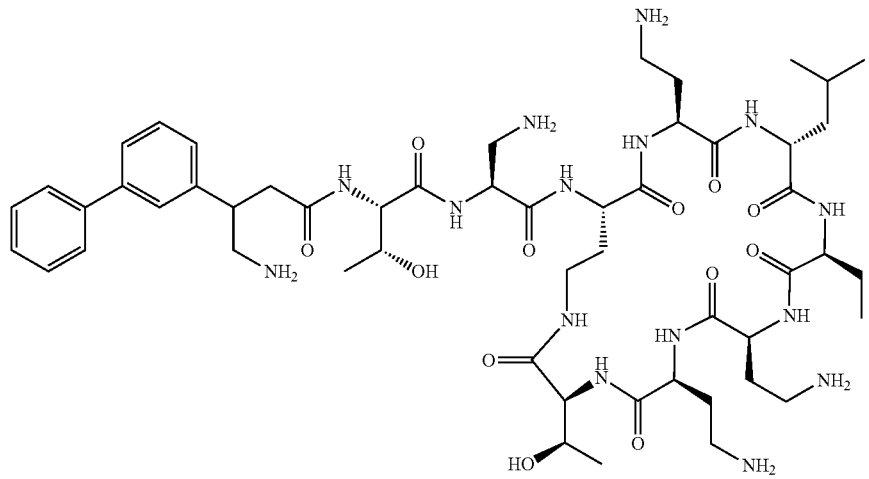 [SMILES: CC[C@@H]1NC(=O)[C@@H](CC(C)C)NC(=O)[C@H](CCN)NC(=O)[C@@H](NC(=O)[C@H](CN)NC(=O)[C@@H](NC(=O)CC(CN)c2cccc(-c3ccccc3)c2)[C@@H](C)O)CCNC(=O)[C@H]([C@@H](C)O)NC(=O)[C@H](CCN)NC(=O)[C@H](CCN)NC1=O]

and salts, solvates, prodrug and protected forms thereof.

3. A pharmaceutical composition comprising a compound according to claim 1 or a salt, solvate, or protected form thereof, optionally together with one or more pharmaceutically acceptable carriers.

4. A method of treating a microbial infection comprising administering to a subject in need thereof a therapeutically effective amount of a compound according to claim 1 or a salt, solvate, or protected form thereof.

5. The method according to claim 4, wherein the infection is a bacterial infection.

6. The method according to claim 5, wherein the bacterial infection is a Gram-negative bacterial infection.

7. The method according to claim 6, wherein the Gram-negative bacterial infection is selected from *Escherichia* spp., *Klebsiella* spp., *Enterobacter* spp., *Salmonella* spp., *Shigella* spp., *Citrobacter* spp., *Morganella morganii, Yersinia pseudotuberculosis* and other Enterobacteriaceae, *Pseudomonas* spp., *Acinetobacter* spp., *Moraxella, Helicobacter, Stenotrophomonas, Bdellovibrio*, acetic acid bacteria, *Legionella* and alpha-proteobacteria.

8. A pharmaceutical composition comprising a compound according to claim 2 or a salt, solvate, or protected form thereof, optionally together with one or more pharmaceutically acceptable carriers.

9. A method of treating a microbial infection comprising administering to a subject in need thereof a therapeutically effective amount of a compound according to claim 2 or a salt, solvate, or protected form thereof.

10. The method according to claim 9, wherein the infection is a bacterial infection.

11. The method according to claim 10, wherein the bacterial infection is a Gram-negative bacterial infection.

12. The method according to claim 11, wherein the Gram-negative bacterial infection is selected from *Escherichia* spp., *Klebsiella* spp., *Enterobacter* spp., *Salmonella* spp., *Shigella* spp., *Citrobacter* spp., *Morganella morganii, Yersinia pseudotuberculosis* and other Enterobacteriaceae, *Pseudomonas* spp., *Acinetobacter* spp., *Moraxella, Helicobacter, Stenotrophomonas, Bdellovibrio*, acetic acid bacteria, *Legionella* and alpha-proteobacteria.

13. A compound of the formula:

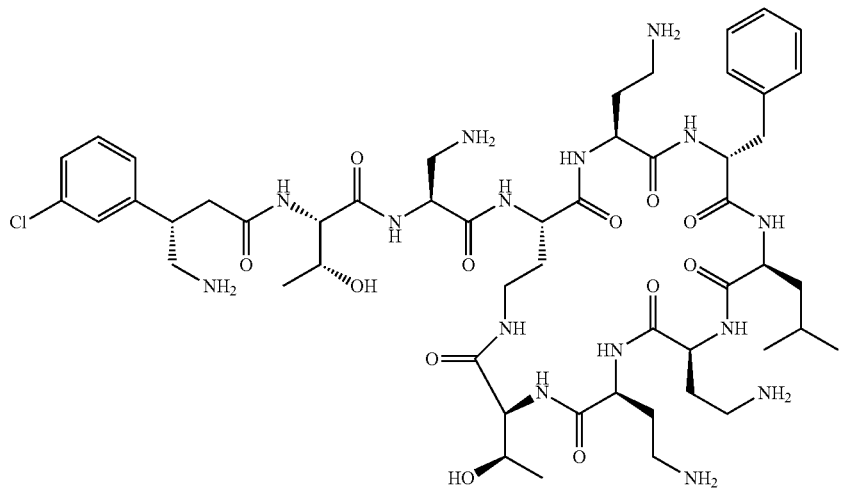 [SMILES: CC(C)C[C@@H]1NC(=O)[C@@H](Cc2ccccc2)NC(=O)[C@H](CCN)NC(=O)[C@@H](NC(=O)[C@H](CN)NC(=O)[C@@H](NC(=O)C[C@H](CN)c2cccc(Cl)c2)[C@@H](C)O)CCNC(=O)[C@H]([C@@H](C)O)NC(=O)[C@H](CCN)NC(=O)[C@H](CCN)NC1=O]

and salts, solvates and protected forms thereof.

14. A compound of the formula:
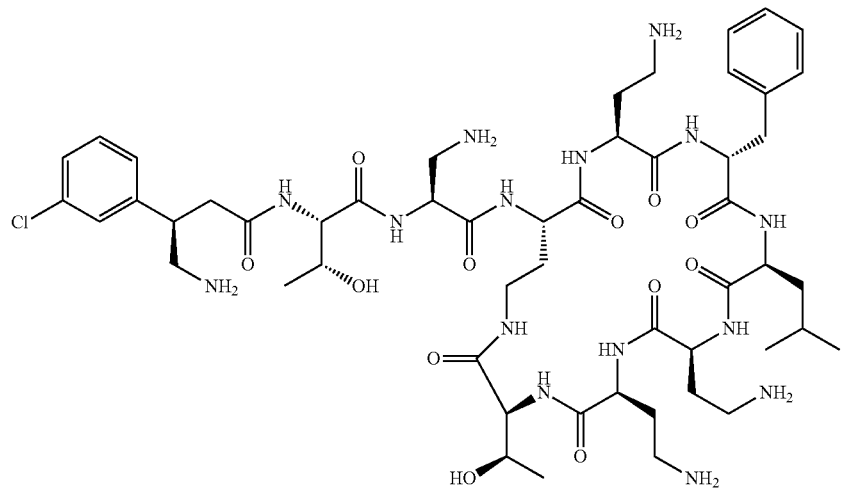 [SMILES: CC(C)C[C@@H]1NC(=O)[C@@H](Cc2ccccc2)NC(=O)[C@H](CCN)NC(=O)[C@@H](NC(=O)[C@H](CN)NC(=O)[C@@H](NC(=O)C[C@@H](CN)c2cccc(Cl)c2)[C@@H](C)O)CCNC(=O)[C@H]([C@@H](C)O)NC(=O)[C@H](CCN)NC(=O)[C@H](CCN)NC1=O]
and salts, solvates and protected forms thereof.
* * * * *